US010233481B2

(12) United States Patent
Marshall et al.

(10) Patent No.: US 10,233,481 B2
(45) Date of Patent: Mar. 19, 2019

(54) MULTI-SAMPLE LASER-SCATTER MEASUREMENT INSTRUMENT WITH INCUBATION FEATURE AND SYSTEMS FOR USING THE SAME

(71) Applicant: BacterioScan LTD, MP Western Galilee (IL)

(72) Inventors: Dana A. Marshall, St. Louis, MO (US); Theodore S. McMinn, St. Louis, MO (US); Dan Vadim Regelman, Kiryat Bialik (IL)

(73) Assignee: BacterioScan LTD, MP Western Galilee (IL)

( * ) Notice: Subject to any disclaimer, the term of this patent is extended or adjusted under 35 U.S.C. 154(b) by 341 days.

(21) Appl. No.: 14/959,054

(22) Filed: Dec. 4, 2015

(65) Prior Publication Data

US 2016/0160260 A1    Jun. 9, 2016

Related U.S. Application Data

(63) Continuation-in-part of application No. 14/562,304, filed on Dec. 5, 2014, now Pat. No. 9,579,648.
(Continued)

(51) Int. Cl.
*C12Q 1/06* (2006.01)
*G01N 33/487* (2006.01)
(Continued)

(52) U.S. Cl.
CPC ............ *C12Q 1/06* (2013.01); *B01L 3/50255* (2013.01); *G01N 21/51* (2013.01); *G01N 33/487* (2013.01);
(Continued)

(58) Field of Classification Search
CPC ............... C12Q 1/06; B01L 3/50255; B01L 2300/0681; B01L 2300/0672;
(Continued)

(56) References Cited

U.S. PATENT DOCUMENTS 3,627,424 A    12/1971   Dorman et al.
3,713,775 A    1/1973    Schmitz
(Continued)

FOREIGN PATENT DOCUMENTS

DE    10128978    12/2002
EP    0320154     6/1989
(Continued)

OTHER PUBLICATIONS

Murray, et al. "Light-scattering methods for antibiotic sensitivity tests", J Clin Pathol, 1980, vol. 33, pp. 995-1001, 8 pages.
(Continued)

*Primary Examiner* — Michael L Hobbs
(74) *Attorney, Agent, or Firm* — Nixon Peabody LLP

(57) ABSTRACT

An optical measurement instrument is an integrated instrument that includes an optical cavity with a light source, a sample cuvette, and an optical sensor. The light source and sensor are on a bench that is on a translational or rotational mechanical platform such that optical beam can be moved to multiple sample containers. The instrument can be used for taking measurements of organism concentration in multiple samples as a production tool for microbiology. Preferably, the instrument holds multiple, individually-loaded, independent fluid samples and determines bacteria concentration via a forward-scattering signal. The instrument can incorporate onboard incubation to promote bacterial growth in the samples during the test. In another aspect, the instrument can be a part of a network for medical diagnostic testing data (Continued)

where data is stored in a manner that is inherently untainted by patient identifiable information.

9 Claims, 17 Drawing Sheets

Related U.S. Application Data

(60) Provisional application No. 62/107,931, filed on Jan. 26, 2015, provisional application No. 62/100,800, filed on Jan. 7, 2015, provisional application No. 62/151,065, filed on Apr. 22, 2015.

(51) Int. Cl.
*G01N 21/51* (2006.01)
*B01L 3/00* (2006.01)
*G01N 21/25* (2006.01)
*G01N 21/47* (2006.01)

(52) U.S. Cl.
CPC . *B01L 2200/0684* (2013.01); *B01L 2300/022* (2013.01); *B01L 2300/043* (2013.01); *B01L 2300/044* (2013.01); *B01L 2300/045* (2013.01); *B01L 2300/0672* (2013.01); *B01L 2300/0681* (2013.01); *B01L 2400/0683* (2013.01); *G01N 21/253* (2013.01); *G01N 2021/4707* (2013.01); *G01N 2201/04* (2013.01)

(58) Field of Classification Search
CPC ....... B01L 2300/0683; B01L 2300/044; B01L 2300/043; B01L 2300/022; B01L 2300/045; G01N 21/51; G01N 21/253; G01N 33/487; G01N 2021/4707; G01N 2201/04
See application file for complete search history.

(56) References Cited

U.S. PATENT DOCUMENTS

| | | | |
|---|---|---|---|
| 3,832,532 A | 8/1974 | Praglin et al. | |
| 3,928,140 A | 12/1975 | Wyatt et al. | |
| 4,066,360 A | 1/1978 | Breddin et al. | |
| 4,101,383 A | 7/1978 | Wyatt et al. | |
| 4,113,386 A | 9/1978 | Lepper, Jr. | |
| 4,119,407 A | 10/1978 | Goldstein et al. | |
| 4,265,538 A | 5/1981 | Wertheimer | |
| 4,577,970 A | 3/1986 | Meserol | |
| 4,754,613 A | 7/1988 | Brito | |
| 4,874,102 A | 10/1989 | Jessop | |
| 4,895,446 A | 1/1990 | Maldari et al. | |
| 5,139,031 A | 8/1992 | Guirguis | |
| 5,187,368 A | 2/1993 | Galante et al. | |
| 5,212,667 A | 5/1993 | Tomlinson, Jr. et al. | |
| 5,351,118 A | 9/1994 | Spinell | |
| 5,386,287 A * | 1/1995 | Berssen | B01L 3/5453 356/246 |
| 5,616,923 A | 4/1997 | Rich et al. | |
| 5,693,944 A | 12/1997 | Rich | |
| 5,969,814 A | 10/1999 | Barber | |
| 5,989,499 A | 11/1999 | Catanzariti | |
| 6,091,483 A | 7/2000 | Guirguis | |
| 6,230,045 B1 | 5/2001 | Hoogenraad et al. | |
| 6,333,008 B1 | 12/2001 | Leistner et al. | |
| 6,515,743 B1 * | 2/2003 | Hayashi | G01N 21/6452 250/458.1 |
| 6,573,992 B1 | 6/2003 | Drake | |
| 6,861,230 B1 | 3/2005 | Murphy et al. | |
| 7,430,046 B2 | 9/2008 | Jiang et al. | |
| 7,961,311 B2 | 6/2011 | Weichselbaum et al. | |
| 8,339,601 B2 | 12/2012 | Weichselbaum et al. | |
| 2003/0036683 A1 | 2/2003 | Kehr | |
| 2003/0048433 A1 | 3/2003 | Desjonqueres | |
| 2004/0070756 A1 | 4/2004 | Rastopov | |
| 2004/0185552 A1 | 9/2004 | Grinner et al. | |
| 2004/0238746 A1 | 12/2004 | Dreyer et al. | |
| 2005/0148085 A1 | 7/2005 | Larsen | |
| 2006/0063146 A1 | 3/2006 | Larsen et al. | |
| 2006/0109476 A1 | 5/2006 | Werner et al. | |
| 2006/0210962 A1 * | 9/2006 | Imaizumi | C12Q 1/04 435/4 |
| 2006/0256338 A1 | 11/2006 | Gratton et al. | |
| 2007/0155017 A1 | 7/2007 | Wyatt | |
| 2007/0159619 A1 | 7/2007 | Chu et al. | |
| 2007/0195324 A1 | 8/2007 | Adams et al. | |
| 2007/0206203 A1 | 9/2007 | Trainer | |
| 2007/0211251 A1 | 9/2007 | Weischselbaum | |
| 2007/0253042 A1 | 11/2007 | Szarvas | |
| 2008/0106737 A1 | 5/2008 | Weichselbaum et al. | |
| 2008/0293091 A1 | 11/2008 | Kanipayor | |
| 2010/0068755 A1 | 3/2010 | Walsh | |
| 2010/0248298 A1 | 9/2010 | Kostrzewa | |
| 2010/0277734 A1 | 11/2010 | Weischselbaum | |
| 2013/0089476 A1 | 4/2013 | Weichselbaum et al. | |

FOREIGN PATENT DOCUMENTS

| | | |
|---|---|---|
| EP | 1136563 | 9/2001 |
| GB | 1515681 | 6/1978 |
| GB | 2412166 | 9/2005 |
| WO | WO 00/09981 | 2/2000 |
| WO | WO 00/66763 | 11/2000 |
| WO | WO 2006/018839 | 2/2006 |
| WO | WO 2013/070948 | 5/2013 |
| WO | WO 2013/153371 | 10/2013 |

OTHER PUBLICATIONS

International Search Report, PCT/IB2015/059385, dated Mar. 17, 2016 (9 pages).
Written Opinion of the International Searching Authority, PCT/IB2015/059385, dated Mar. 17, 2016 (8 pages).

* cited by examiner

MULTI-SAMPLE LASER-SCATTER MEASUREMENT INSTRUMENT WITH INCUBATION FEATURE AND SYSTEMS FOR USING THE SAME

RELATED APPLICATIONS

The present application claims priority to (i) U.S. Provisional Application Ser. No. 62/107,931, filed Jan. 26, 2015, titled "Multi-Sample Laser-Scatter Measurement Instrument With Incubation Feature" (ii) U.S. Provisional Application Ser. No. 62/100,800, filed Jan. 7, 2015, titled "System And Method For Detecting and Identifying Bacteria Type in a Fluid Sample," (iii) U.S. Provisional Application Ser. No. 62/151,065, filed Apr. 22, 2015, titled "Networked Biological Data Collection System For Use With Laser-Scatter Measurement Instruments," and (iv) U.S. application Ser. No. 14/562,304 now U.S. Pat. No. 9,579,648 issued on Feb. 8, 2017, titled "Cuvette Assembly Having Chambers for Containing Samples to be Evaluated through Optical Measurement," filed on Dec. 5, 2014, each of which is herein incorporated by reference in entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever

FIELD OF THE INVENTION

The present invention relates generally to the field of measurements of biological liquid samples. Specifically, the present invention relates to systems and method for determining whether bacteria are present in a liquid sample and, if so, for determining the effect of chemoeffectors on the bacteria within the liquid sample.

BACKGROUND OF THE INVENTION

Many applications in the field of analytical research and clinical testing utilize methods for analyzing liquid samples. Among those methods are optical measurements that measure absorbance, turbidity, fluorescence/luminescence, and optical scattering measurements. Optical laser scattering is one of the most sensitive methods, but its implementation can be very challenging, especially when analyzing biological samples in which suspended particles are relatively transparent in the medium.

One particle that often requires evaluation within a liquid is bacteria. The presence of bacteria is often checked with biological liquids, such as urine, amniotic, pleural, peritoneal and spinal liquids. In a common analytical method, culturing of the bacteria can be time-consuming and involves the use of bacterial-growth plates placed within incubators. Normally, laboratory results take may take a day or several days to determine whether the subject liquid is infected with bacteria and the type of bacteria.

Quantification of bacteria, yeast, and other organisms in fluid can be useful for medical diagnosis, drug development, industrial hygiene, food safety, and many other fields. Measurement of light scattering and absorption in samples is a known method for approximating the concentration of organisms. For example, techniques for detecting and counting bacteria are generally described in U.S. Pat. Nos. 7,961, 311 and 8,339,601, both of which are commonly owned and are herein incorporated by reference in their entireties.

Accordingly, there is a need for an improved systems and methods that quickly determine whether bacteria is present in the fluid sample and determine the effect of chemoeffectors on a fluid sample. There is also a need for an improved systems and methods that more quickly determine the type of bacteria after it is determined that bacteria is present.

Regarding the data collection from medical testing, there are a wide variety of tests conducted in medical labs using collected patient specimens. These tests, performed "in vitro" can include physical, chemical, and microbiology measurements to determine patient state of health, or to advise a care path. Commonly, these tests are conducted in instruments or workstations that autonomously generate measurements and interpreted results. Results are issued by report to a proximate user in the lab (e.g., a lab operator), and may be collected by one of a variety of available general-purpose Laboratory Information Systems ("LIS") that manage lab reporting and billing, and can be thereby be viewed by a doctor or other user at a location away from the instrument (a remote user). By this method, the lab is able to communicate the interpreted results from a variety of tests and instruments to users for any individual patient as part of the patient care record, to archive the results in a findable location indexed by the patient identity, and to record the activities for billing and other purposes.

In these installations, the central database for the LIS does not assist in the interpretation of the data, or impact the algorithms of interpretation for the instruments. In operation, a test or instrument may typically process the sample in a container or disposable which is directly marked, tagged or labeled, or otherwise uniquely affiliated with a test event identifier or Accession Number. The test data is generally retrieved from the instrument in its fully interpreted form, and is directly indexed to a unique test event identifier, such as the lab Accession Number. This record may also include patient information such as age, gender, specifics of health and care, location, and date. For some combinations and circumstances, this information could be correlated to create patient identifiable and private data, thereby requiring the LIS to be designed, operated, and maintained in such a way that such information retains its security in accordance with privacy law. Additionally, results from tests are generally indexed to a test identifier such as lab Accession Number, and recorded in the patient care record along with other private information, and therefore this data can also be considered a potentially a privacy/security concern.

There is also a need for an improved systems and methods to create a data network that can be used to collect and store medical diagnostic data in a way that is inherently immune to privacy concerns because no single database contains both the test data with any private data or collection of data which could be combined to create private data or be construed to constitute Patient Identifiable Information ("PII"). At the same time, the network includes secure software to retrieve, analyze, and correlate data from individual tests from the various databases to thus momentarily create an interpreted result, indexed to the accession identifier, and which can be delivered in digital or printed in hard copy form for the user or LIS, and which is then deleted from the system with no enduring record. In one preferred embodiment, the instruments used within the network that create data include the instruments testing for the presence and concentration of bacteria from laser scattering (or from optical instruments measuring the absorbance, turbidity, fluorescence/luminescence, and optical scattering of fluids). The data from these instruments is stored in a separate database than a database having any PII. The data may include the results of various chemoeffectors on a liquid sample containing bacteria.

SUMMARY OF THE INVENTION

The present invention includes several instruments for taking measurements of organism concentration in multiple samples as a production tool for microbiology. A first instrument holds multiple, individually-loaded, independent fluid samples and determines bacteria concentration via a forward-scattering signal. The instrument can incorporate onboard incubation to promote bacterial growth in the samples during the test.

The instrument is preferably an integrated instrument that includes an optical cavity with a light source, a sample cuvette, and an optical detector. All are enclosed within a light-tight enclosure. The light source and sensor/detector are on a bench that is on a translational mechanical stage such that optical beam can be moved to multiple sample containers by mechanical or optical mechanisms and components.

In another embodiment of the first instrument, there is a fixed optical beam and the multiple samples can be moved sequentially into the optical beam by being translated. Or, the multiple samples can be moved sequentially into the optical beam because the samples are configured around a pivot point and can be rotated into a beamline for sequential measurement. In both embodiments, the sample container is preferably held in close proximity to a source of heat that is thermostatically controlled to provide incubation warmth to the liquid sample contained.

Alternatively, the present invention is an optical measuring instrument for determining a concentration of bacteria in a plurality of fluid samples. The instrument comprises a housing, a plurality of fluid containers, a light source, at least one sensor, and a heating element. The housing has a substantially light-tight enclosure. Each of the fluid containers holds a corresponding one of the plurality of fluid samples. Each of the fluid containers has an input window and an output window. The light source within the housing provides an input beam for transmission into the input windows of the fluid containers and though the corresponding fluid samples. The input beam creates a forward-scatter signal associated with the concentration of bacteria. The at least one sensor within the housing detects the forward-scatter signal exiting from the output windows. The heating element within the housing maintains the fluid samples at a desired temperature to encourage bacterial growth in the fluid samples over a period of time. At least one of the input beam and the fluid containers are movable relative to each other so that the input beam sequentially addresses each of the plurality of fluid samples.

In yet a further aspect, the present invention is a method of determining the concentration of bacteria in a plurality of fluid samples by use of an optical measuring instrument. The method comprises, within the optical measuring instrument, incubating the fluid samples while each of the fluid samples is within a corresponding one of a plurality of cuvette chambers. Each cuvette chamber has a first window for receiving an input beam and a second window for transmitting a forward-scatter signal caused by the input beam. The method further comprises during the incubating, repeatedly transmitting the input beam through each of the fluid samples and measuring a series of forward-scatter signals for each of the fluid samples, and determining that at least one fluid sample includes a concentration of bacteria in response to changes in the forward-scatter signals within the series of forward-scatter signals for the at least one fluid sample.

Alternatively, the present invention is an optical measuring instrument for determining a concentration of bacteria in a plurality of fluid samples. The instrument includes a plurality of cuvette assemblies having optical chambers for receiving a respective one of the plurality of liquid samples. Each of the optical chambers includes an entry window for allowing transmission of an input light beam through the respective liquid sample and an exit window for transmitting an optical signal caused by the bacteria within the respective liquid sample. Each cuvette assembly has a first pair of registration structures associated therewith. The instrument also includes a platform structure with multiple second pairs of registration structures for mating with the first pair of registration structures of the plurality of cuvette assemblies. The instrument further includes a light source producing the input light beam and a sensor for receiving the optical signal caused by the bacteria.

In yet another aspect, the present invention is an optical measuring instrument for determining a concentration of bacteria in a plurality of fluid samples. The instrument comprises a plurality of cuvette assemblies having optical chambers for receiving a respective one of the plurality of liquid sample. Each of the optical chambers includes an entry window for allowing transmission of an input light beam through the respective liquid sample and an exit window for transmitting an optical signal caused by the bacteria within the respective liquid sample. The instrument includes a heating system that permits a controlled incubation of the fluid samples. The instrument also includes a light source for producing the input light beam and a sensor for receiving the optical signal. The light source being periodically operational during the controlled incubation so as to allow the sensor to receive a series of optical signals that are used for determining the concentration of bacteria within each of the plurality of fluid samples.

The present invention can also be considered to be an optical measurement system for use in optically measuring bacteria within a liquid sample. The instrument comprises (i) a light source for producing the input beam, (ii) a sensor for receiving a forward-scatter signal caused by the input beam passing through a container containing the fluid sample with the bacteria, (iii) a heating system that permits a controlled incubation temperature for the fluid sample, and (iv) a moveable optical bench. The light source and the sensor are mounted on the optical bench and the movement of the optical bench permits the fluid sample to be placed into a path of the input beam.

In another aspect, the present invention is a system and method that (i) detects the presence of bacteria in a liquid sample, (ii) determines when a certain bacteria concentration is present in the liquid sample, and (iii) in response to a predetermined bacteria concentration being present, identifies the type of bacteria through use of a microbial identification device. An optical measurement system has fluid-sample-holding cuvettes (preferably multi-chamber cuvettes) and on-board incubation functionality, such that it can detect the presence of the bacteria and incubate the fluid sample until the predetermined bacterial concentration is detected in the fluid sample. The optical measurement system preferably uses cuvettes that receive an input laser beam through one window and transmit through another window a forward-scatter signal indicative of the bacterial concentration within the fluid sample.

In another aspect, the present invention is a method of identifying bacteria in a fluid sample, comprising (i) placing the fluid sample in a cuvette having a first window for receiving an input beam and a second window for transmitting a forward-scatter signal indicative of the presence or absence of the bacteria in the fluid sample, (ii) incubating the fluid sample in the cuvette within an optical-measuring instrument that provides the input beam, (iii) passing the input beam through the fluid sample while the cuvette is in the optical-measuring instrument, (iv) analyzing the forward-scatter signal from the fluid sample, (v) in response to the forward-scatter signal indicating the presence of bacteria in the fluid sample, continuing to incubate the fluid sample within the optical-measuring instrument to increase the concentration of the bacteria within the fluid sample and at least partially identify the type of bacteria within the fluid sample.

In yet a further aspect, the present invention relates to a network for medical diagnostic testing data where data is stored in a manner that is inherently untainted by patient identifiable information or any collection of data that might be construed to be private patient information. Data from instruments networked within such a system may be transmitted, stored, aggregated, analyzed, and re-interpreted without concern about patient privacy or data security, reducing the burdens of database and network design, operation, maintenance and use.

In an alternative aspect, the present invention is a method of identifying bacteria in a fluid sample, comprising (i) placing the fluid sample in a cuvette having a first window for receiving an input beam and a second window for transmitting a forward-scatter signal indicative of the presence of the bacteria in the fluid sample, (ii) in response to a first forward-scatter signal indicating the presence of bacteria, incubating the fluid sample in the cuvette to increase the bacteria concentration, (iii) in response to a second forward-scatter signal indicating a predetermined concentration of bacteria, removing, from the cuvette, the fluid sample having the increased concentration of bacteria and (iv) placing at least a portion of the bacteria removed from the cuvette in a mass-spectrometry microbial identification device to identify the type of bacteria.

Alternatively, the present invention is a network for collecting and using biological data, comprising a plurality of instruments, a first database, second database, report-generator software module, and a data-mining software module. The plurality of instruments are at remote locations and each of the plurality of instruments tests a fluid sample from a patient. The first database stores a set of raw test data for each fluid sample from the plurality of instruments. Each set of raw test data is stored in a manner that is indexed to a test sample ID. The first database lacks any private patient information. The second database stores an event record that associates the test sample ID and a patient ID. The report-generator software module accesses information from the first database and the second database to develop a test report for each patient. The data-mining software module accesses information from only the first database to determine or predict trends from the raw test data.

In another aspect, the invention is a method of collecting and using biological information from a plurality of instruments at different locations. The method comprises (i) testing a plurality of fluid samples from a plurality of patients by use of the plurality of instruments, (ii) storing, in a first database, a set of raw test data for each of the plurality of fluid samples, such that each set of raw test data is indexed to a test sample ID, (iii) storing, in a second database, each of the test sample IDs in a manner that is correlated to a patient ID; (iv) accessing, by use of a report-generator software module, information from both the first database and the second database to develop a report for the patient; and (v) performing, by use of a data-mining software module, analytics on the sets of raw test data store in the first database.

In another aspect, the present invention is a network for collecting and using biological data related to bacteria within fluid samples, comprising a plurality of instruments that are at remote locations. Each of the plurality of instruments for testing a forward-scatter signal that is used to determine the presence of bacteria in a fluid sample from a patient. The network includes a first database for storing a set of raw test data for each fluid sample from the plurality of instruments. Each set of raw test data is stored in a manner that lacks private patient information. The network also includes a data-mining software module that accesses information from only the first database to determine or predict trends from the raw test data related to at least one of the group consisting of: (i) a direct comparison of multiple antibiotics against a certain infection, (ii) a direct comparison of the same antibiotic at different concentrations against a certain infection, (iii) a direct comparison of a new drug against known drugs, (iv) an indication of or a detection of an emergence of one or more incidents of resistant infection in any healthcare site or geographic region, (v) an indication of or a detection of a certain type of bacteria has become or may be becoming resistant to a certain antibiotic, (vi) an indication of or a detection of a certain type of bacteria in a certain geographical region has become or may be becoming resistant to a certain antibiotic, (vii) an indication of or a detection of a certain type of bacteria in a certain hospital or care unit has become or may be becoming resistant to a certain antibiotic, (viii) an indication of or a detection of the susceptibility or resistance of an infection pathogen to an antimicrobial agent, molecule, or combination or sequence of exposure of antimicrobial agent or molecule with or without the active involvement of the proximate healthcare providers or clinical microbiologist.

Additional aspects of the invention will be apparent to those of ordinary skill in the art in view of the detailed description of various embodiments, which is made with reference to the drawings, a brief description of which is provided below.

Figure 1A:
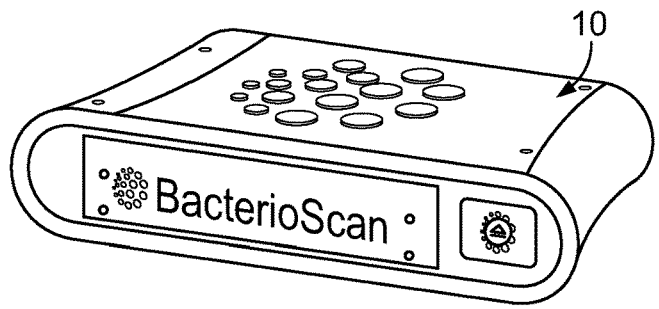
FIG. 1A illustrates an optical-measuring instrument that is capable of incubating fluid samples by having a controlled internal heating system.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

FIG. 1A illustrates an optical measuring device 10 (manufactured by the assignee of the present application as the BacterioScan 216R instrument) that can rapidly detect and quantify the concentration of bacteria in a fluid sample. As discussed in more detail below, the instrument 10 includes on-board incubation, such that reagents to enhance growth are not necessarily needed (although they can be used). The instrument 10 uses laser-scattering technology to quantify bacteria growth in fluid sample sizes as small as 1 ml. In particular, the instrument 10 transmits a laser beam through a fluid sample, and measures the scatter signal caused by the bacteria in the fluid sample, preferably through a forward-scattering measurement technique. The on-board incubation provides for fluid sample temperatures ranging from room temperature up to 42° C. (or higher). The instrument 10 permits for a range of optical measurement intervals over a period of time (e.g., 1-6 hours) to determine the growth and concentration of the bacteria within the liquid samples during incubation. The optical measuring instrument 10 can detect and count bacteria by various techniques that are generally described in U.S. Pat. Nos. 7,961,311 and 8,339,601, both of which are commonly owned and are herein incorporated by reference in their entireties.

Figure 1B:
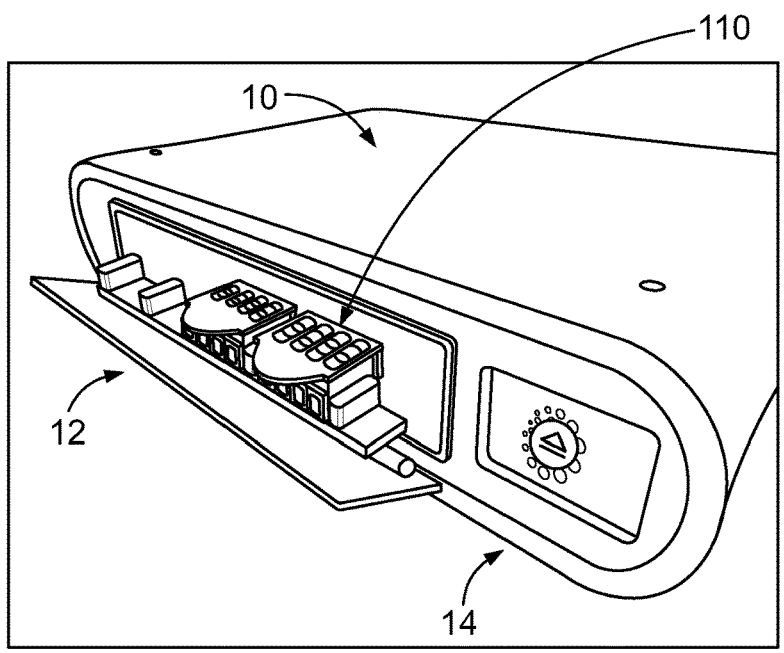
FIG. 1B illustrates the cuvettes of FIG. 2 being placed and registered within the optical-measuring instrument of FIG. 1A.

FIG. 1B illustrates cuvette assemblies 110 being inserted into the optical measurement instrument 10 of FIG. 1A. To do so, a front door 12 on the optical measurement instrument 10 is opened and the cuvette assemblies 110 are placed on a registration and orientation plate or platform 210 (See FIG. 8) such that the laser-input window and output-signal window of each cuvette (FIGS. 6-7) are substantially registered within the optical measurement instrument 10, permitting periodic optical measurements to be taken of each sample. As shown, the optical measurement instrument 10 may include up to four cuvettes 110, such that 16 different samples can be tested periodically through the optical measurement instrument 10.

The optical measuring instrument 10 includes a display device 14 that provides information regarding the tests and/or fluid samples. For example, the display device 14 may indicate the testing protocol being used for the samples (e.g., time and temperature) or provide the current temperature within the instrument 10. Preferably, the display device 14 also includes an associated touchscreen input (or a different set of input buttons can be provided) that allows a user to perform some of the basic functions of the instrument 10, such as a power on/off function, a door open/close function, a temperature increase/decrease function, etc.

Figure 2:
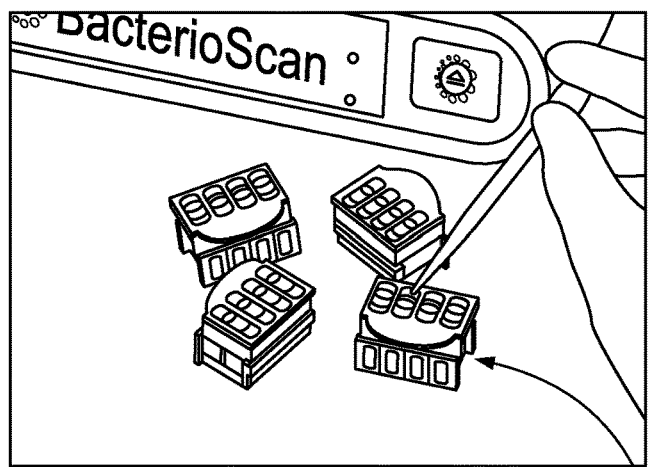
FIG. 2 illustrates four multi-chamber cuvettes that receive fluid samples that are placed in the optical-measuring device of FIGS. 1A and 1B.

FIG. 2 illustrates four cuvettes assemblies 110, each of which has four openings leading to four different chambers that provide for optical measurement of the fluid samples in the four chambers. The optical measurement is preferably a forward-scattering signal measurement caused by bacteria in the fluid sample. The cuvette assemblies 110 are described in more detail in U.S. Publication No. 2015-0160119, titled "Cuvette Assembly Having Chambers for Containing Samples to be Evaluated through Optical Measurement," filed on Dec. 5, 2014, which is commonly owned and is hereby incorporated by reference in its entirety. A brief description of the cuvette assembly 110 is provided below with reference to FIGS. 6-8. The cuvette assemblies 110 can be filled with fluid samples automatically or manually. As shown, the cuvette assemblies 110 are filled through the use of a pipette.

Figure 3:
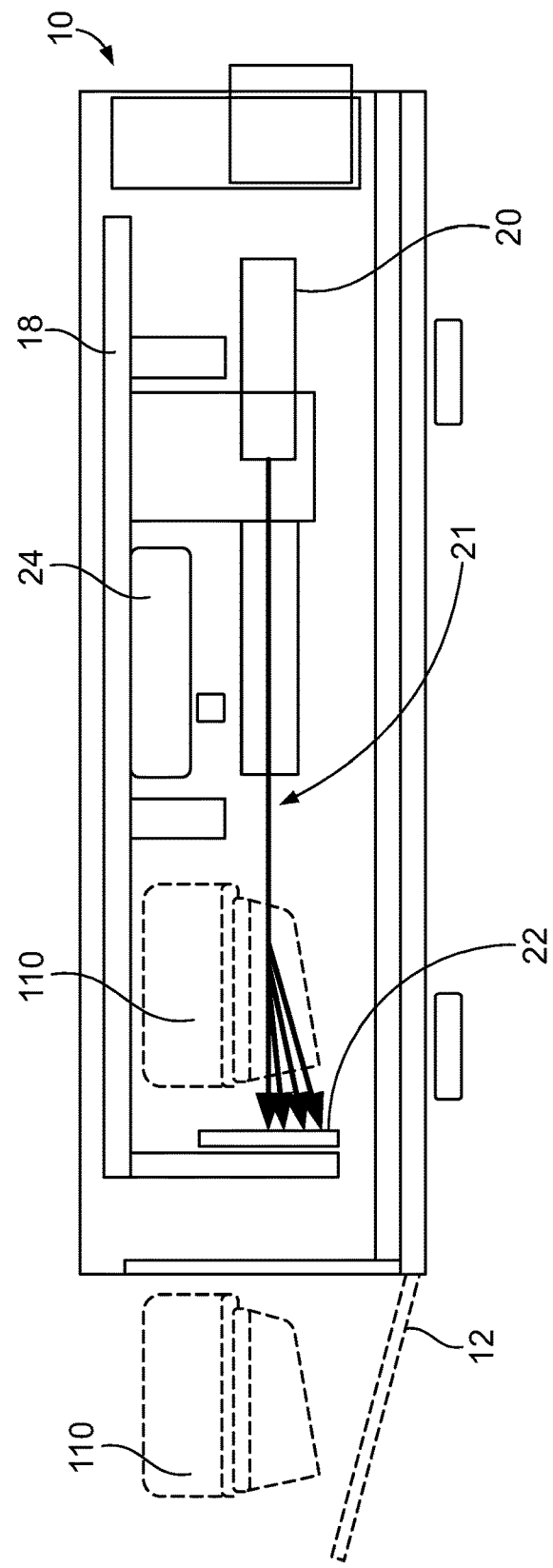
FIG. 3 illustrates a side view of the optical-measuring instrument of FIGS. 1A and 1B.
Figure 4:
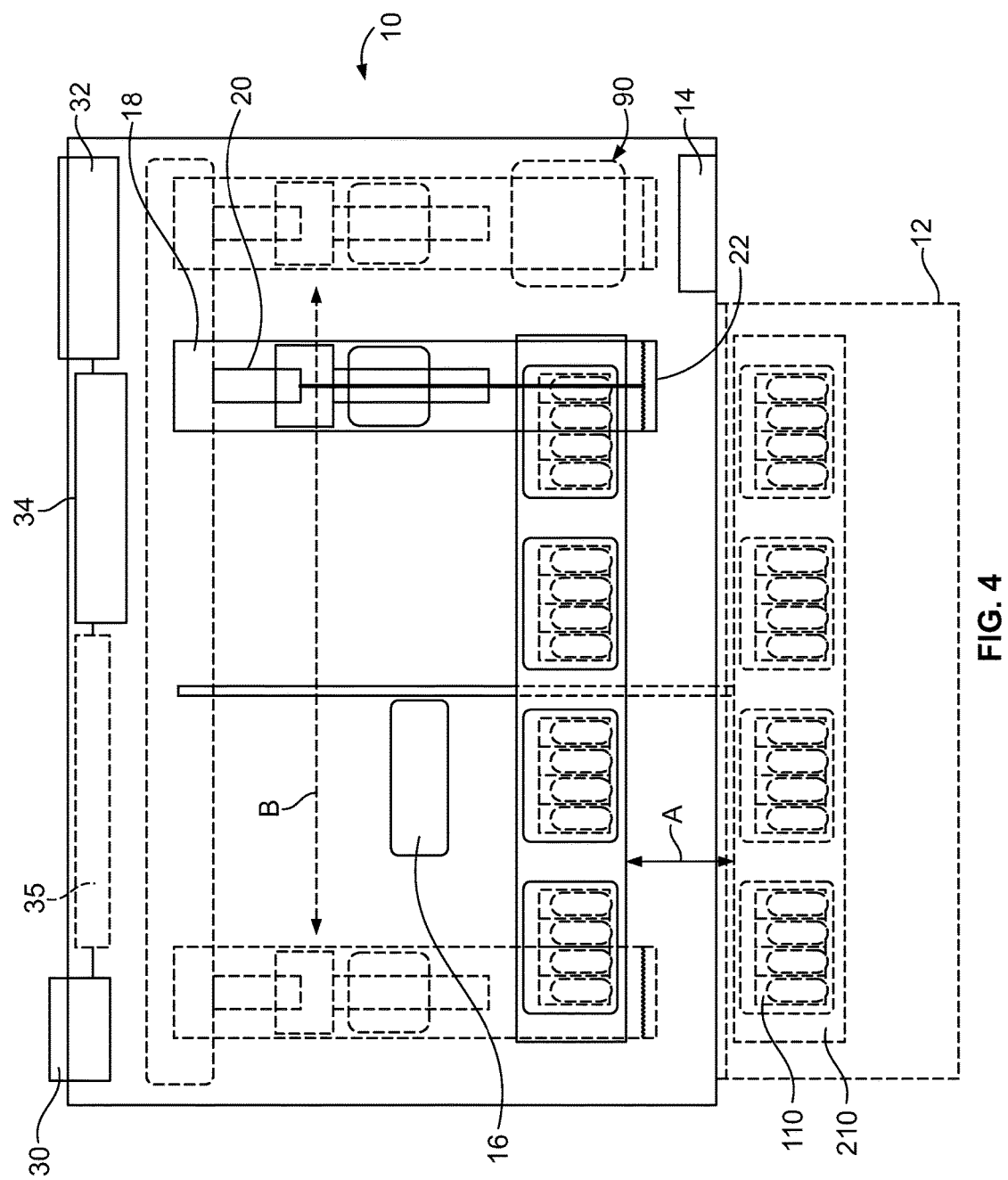
FIG. 4 illustrates a top view of the optical-measuring instrument of FIGS. 1A and 1B.

FIGS. 3-4 illustrate more of the details of the internal structures and components of the optical measurement instrument 10. In particular, as shown best in FIG. 4, the cuvettes assemblies 110 are loaded onto a movable platform 210 (show in detail in FIG. 8) when the door 12 is opened. Once loading is complete, the platform 210 moves inwardly into the instrument 10 and the door 12 is rotated to the closed position, creating a substantially light-tight seal. The door 12 has seals and/or gaskets around it so that the instrument 10 provides a light-tight enclosure to ensure proper signal detection by the sensor 22. As such, the movable platform 210 translates back and forth in the direction of arrow "A" in FIG. 4. The instrument 10 includes a motor 16, such as a motor that operates a gear (e.g., a worm gear) that is actuated to perform the platform movement and the opening and closing of the door 12.

An optical bench 18 is located within the instrument 10. A laser 20 (a light source), which provides an input beam 21, and a sensor 22 are coupled to the optical bench 18 in a fixed orientation. In one embodiment, the laser 20 is a visible wavelength collimated laser diode. In another embodiment the laser 20 is a laser beam delivered from an optical fiber. In yet another embodiment, the laser 20 includes multiple wavelength sources from collimated laser diodes that are combined into a single co-boresighted beam through one of several possible beam combining methods. In another example, the light source 20 is an incoherent narrow wavelength source such as an Argon gas incandescent lamp that is transmitted through one or more pinholes to provide a beam of directionality. A stepper motor 24 provides translation movement in the direction of arrow "B" to the optical bench 18, such that the laser 20 and the sensor 22 can move from side to side so as to be registered in 16 discrete positions that correspond to the 16 samples within the four cuvettes assemblies 110. At each position, the laser 20 is operational and its input beam 21 causes a forward-scatter signal associated with the liquid sample in question. The forward-scatter signal is detected by the sensor 22 and is associated with the bacteria concentration. As explained in more detail below with respect to cuvettes assemblies 110, each sample undergoes some type of filtering within the cuvette assembly 110 and/or outside the cuvette assembly 110 such that unwanted particles are substantially filtered, leaving only (or predominantly only) the bacteria. Due to the incubation feature within the instrument 10, the necessary environment around the cuvette assemblies 110 can be controlled to promote the growth of the bacteria, such that subsequent optical measurements taken by the combination of the laser 20 and the sensor 22 results in a stronger forward-scatter signal indicative of increased bacterial concentration. The instrument 10 includes internal programming that (i) controls the environment around the fluid sample and (ii) dictates the times and/or times-intervals between optical measurements to determine whether the bacteria has grown and, if so, how much the concentration of bacteria has increased. The output of the instrument 10 can be seen on a separate display, as shown in FIGS. 11-12.

Figure 6:
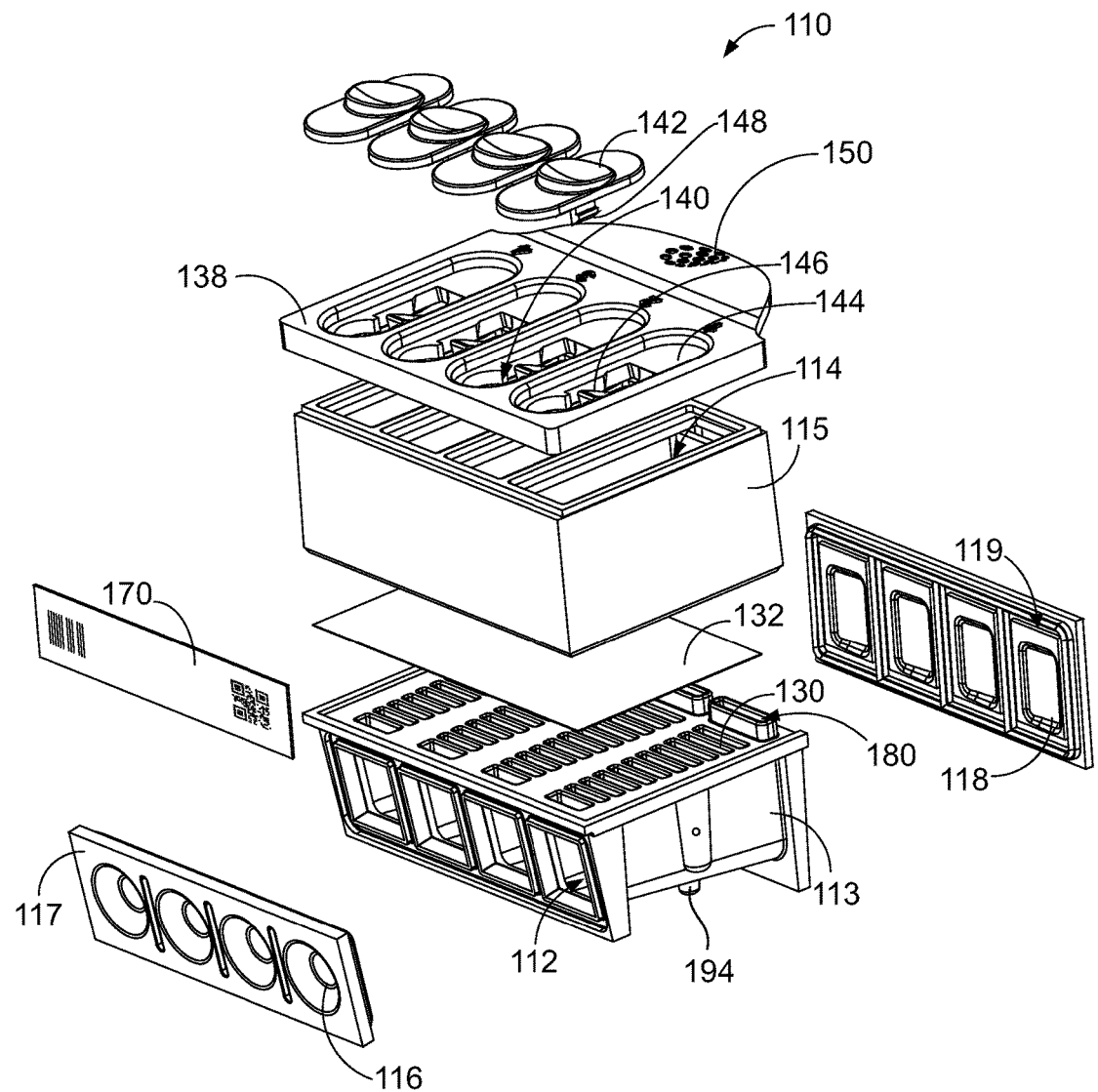
FIG. 6 is an exploded view of one the multi-chamber cuvettes of FIG. 2 that is used with the optical-measuring device of FIGS. 1A and 1B.
Figure 11:
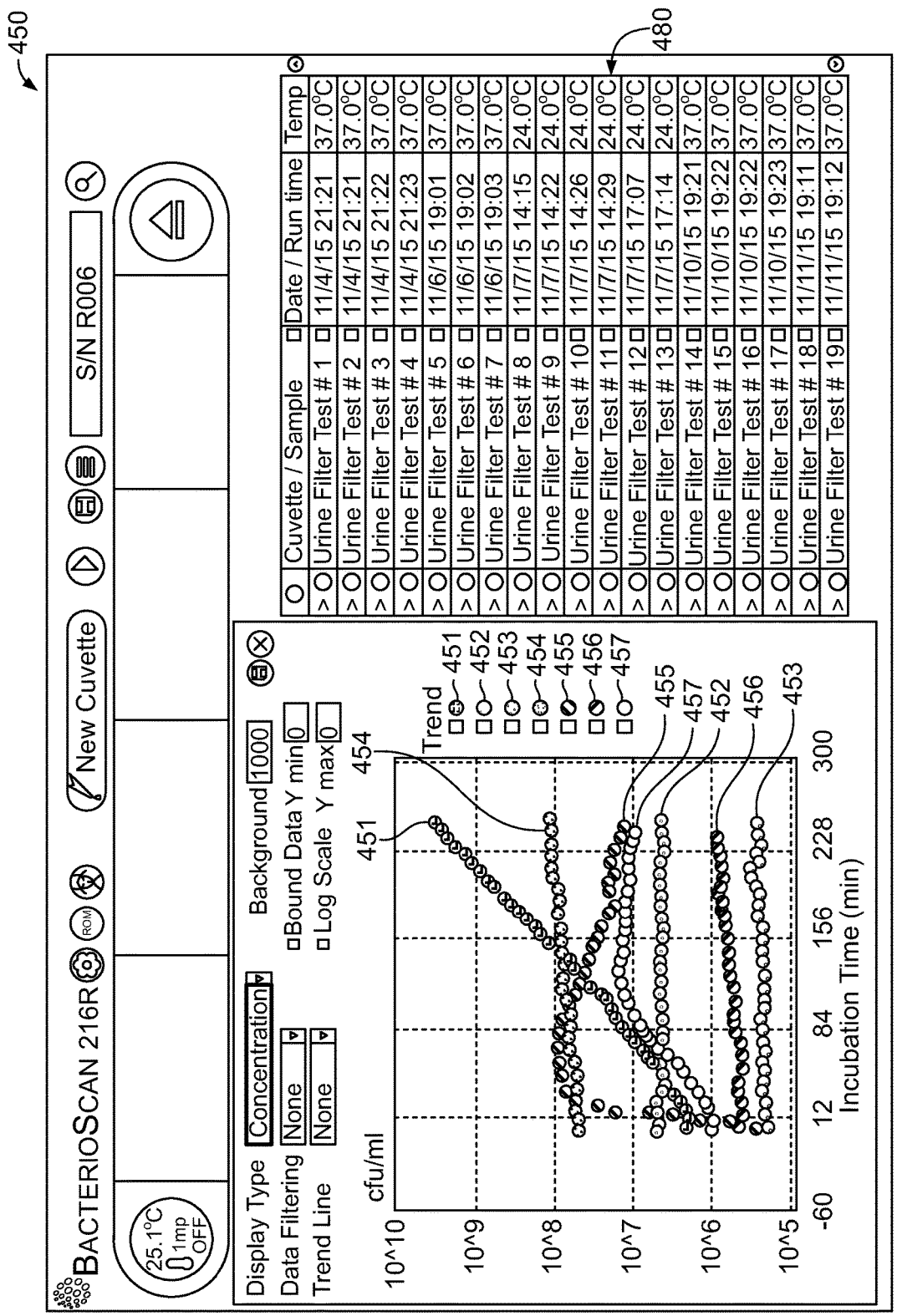
FIG. 11 is an image of a display device during operation of instrument of FIG. 1, which includes bacterial growth curves for seven different fluid samples over a 240-minute period.
Figure 12:
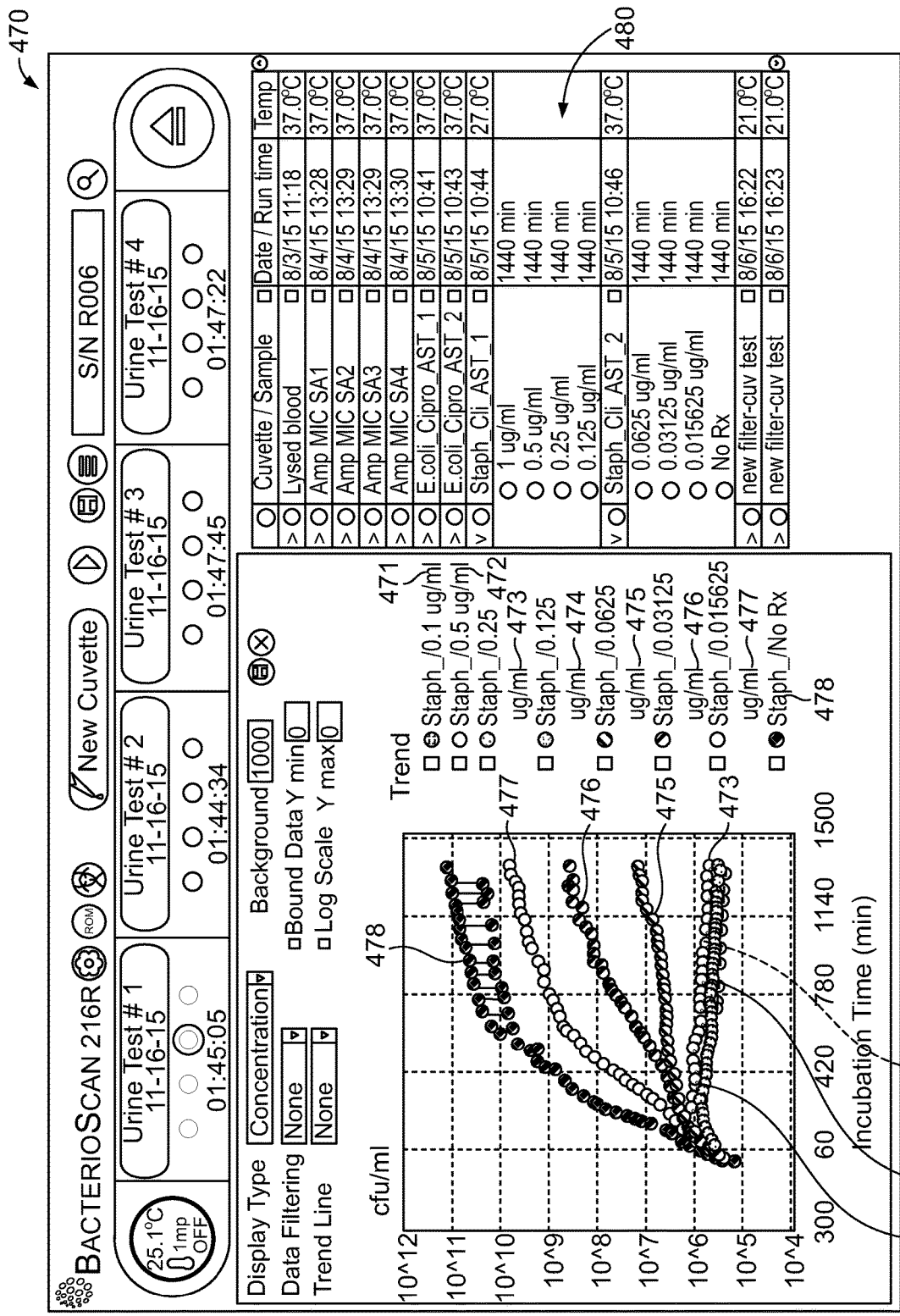
FIG. 12 is another image of a display device during operation of the instrument of FIG. 1 over a 1300-minute period, wherein the bacterial growth curves are for eights samples derived from a single fluid sample but having different antibiotic concentrations.

In addition to the display 14 located on the instrument 10 (and preferably the input buttons and/or touchscreen on the instrument 10), the instrument 10 also includes a port 30 (e.g., a USB connection port) for communication with an external device such as a general purpose computer that would be coupled to the display, such as the one shown in FIGS. 11-12. The instrument 10 can receive instructions from an external device that control the operation of the instrument 10. The instrument 10 can also transmit data (e.g., forward-scatter signal data, test-protocol data, cuvette-assembly data derived from a coded label 170 as shown in FIG. 6, diagnostic data, etc.) from the port 30. The instrument 10 also includes an input power port 32 (e.g., A/C power), which is then converted into a DC power supply 34 for use by the motors, laser, sensors, and displays, etc. One or more printed circuit boards 35 provide the various electronics, processors, and memory for operating the instrument 10.

Figure 5:
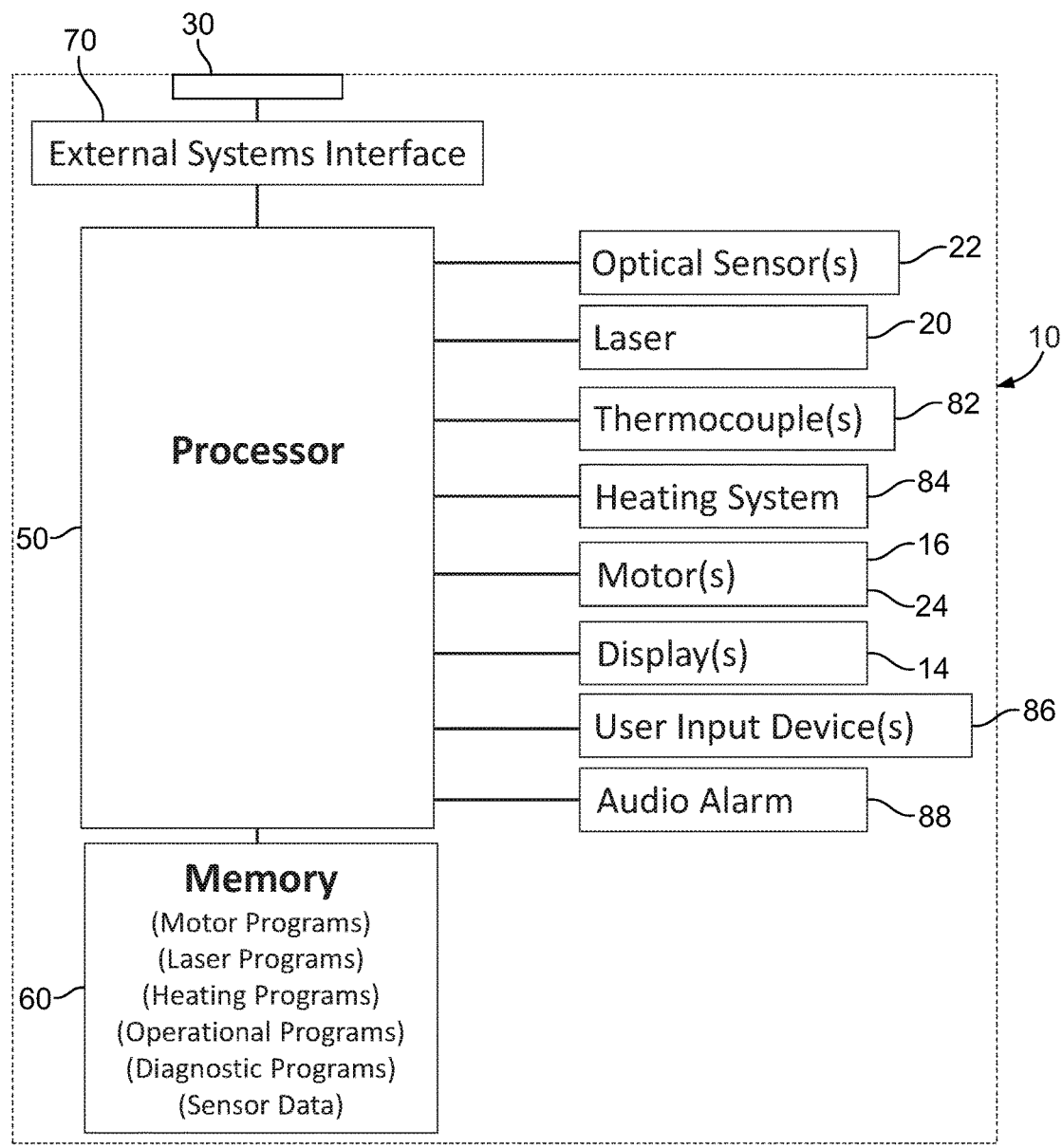
FIG. 5 illustrates a system control diagram for the optical-measuring instrument of FIGS. 1A and 1B.

FIG. 5 illustrates one embodiment for a control system that is located within the instrument 10. The instrument 10 includes one or more printed circuit boards 35 that include at least one processor 50 (and possibly several processors) and at least one memory device 60. The processor 50 communicates with the memory device 60, which includes various programs to operate the motor(s), the laser, the sensors, the heating system, the basic operational functionality, diagnostics, etc. The processor 50 is in communication with the functional components of the instrument 10, such as (1) the optical sensor(s) 22 that sense the forward-scatter signals (or other optical signals, such as fluorescence signals), (2) the laser 20 or other light source that creates the light beam 21 is transmitted into the cuvettes, (3) thermocouple sensors 82 that determine the temperature within the enclosure (or associated with the surface of the cuvette, (4) the heating system 84, such as Kapton heaters, IR heaters, etc., which are preferably placed on the platform or tray 210 (FIG. 8) on which the cuvettes reside, (5) the motors 16, 24 used for opening the door, moving the platform, and moving the optical bench, (6) the display(s) 14 on the front of the instrument, (7) any user input devices 86 (mechanical buttons or touchscreens), and (8) an audio alarm 88 to alert the operator of the instrument to a particular condition or event (e.g., to indicate that one or more samples have reached a certain testing condition, such as a high bacterial concentration, a certain slope in a bacterial-growth curve has been achieved, or a certain forward-scatter signal exceeds a certain value).

The processor 50 is also communicating with an external systems interface 70, such as interface module, associated with the output port 30 on the instrument 10. The primary functions of the processor(s) 50 within the instrument 10 are (i) to maintain the enclosure within the instrument 10 at the appropriate temperature profile (temperature versus time) by use of the thermocouples 82 and heating system 84, (ii) to sequentially actuate the laser 10 so as to provide the necessary input beam 21 into the samples within the cuvette assemblies 110, (iii) to receive and store/transmit the data in the memory device 60 associated with the optical (e.g., forward-scatter) signals from the sensor(s) 22, and (iv) to analyze the forward-scatter signals to determine the bacterial concentration. Alternatively, the control system or computer module that controls the instrument 10 could be partially located outside the instrument 10. For example, a first processor may be located within the instrument 10 for operating the laser, motors, and heating system, while a second processor outside the instrument 10 handles the data processing/analysis for the forward-scatter signals received by the sensor 22 to determine bacterial concentration. The test results (e.g., bacterial concentration indication) and data from the instrument 10 can be reported on the instrument display 14 and/or transmitted by USB, Ethernet, wifi, Bluetooth, or other communication links from the external systems interface 70 within the instrument 10 to external systems that conduct further analysis, reporting, archiving, or aggregation with other data (such as the network 600 in FIG. 19). Preferably, as discussed in more detail relative to FIGS. 19-22, a central database receives test results and data from a plurality of remotely located instruments 10 such that the test data and results (anonymous data/results) can be used to determine trends using analytics, which can then be used to derive better and more robust operational programs for the instrument 10 (e.g., to decrease time per test, or decrease the energy of the tests by used lower incubation temperatures).

Figure 7:
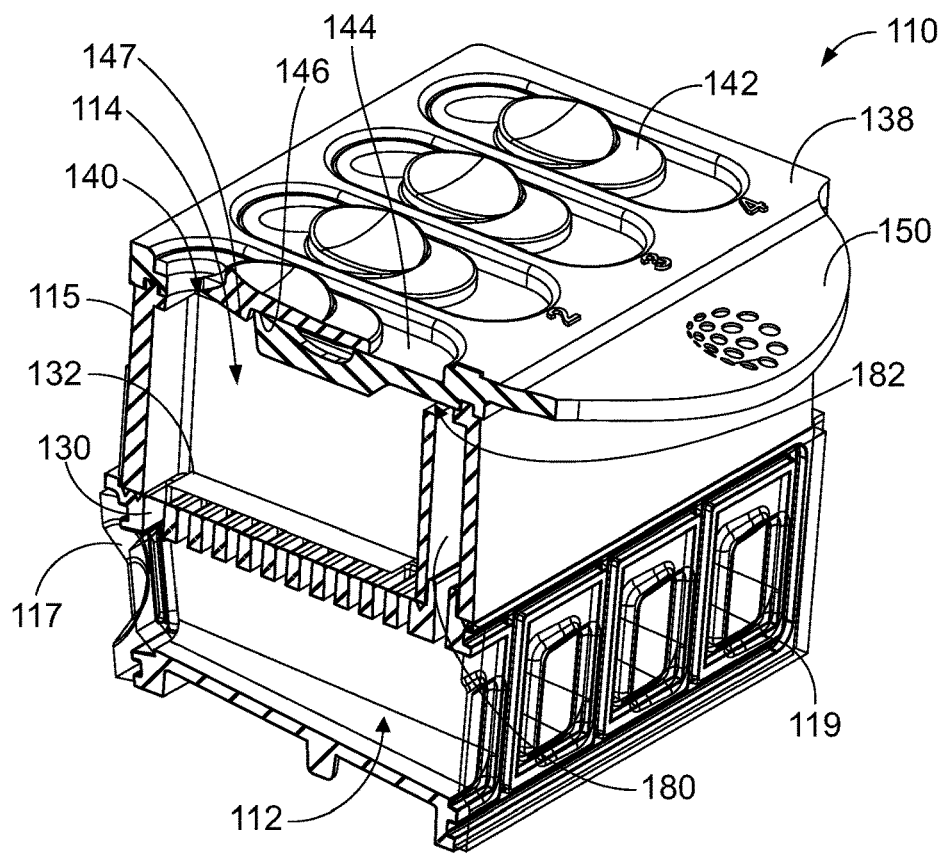
FIG. 7 is a cross-sectional view through one chamber of the multi-chamber cuvette of FIG. 2 that is used with the optical-measuring device of FIGS. 1A and 1B.

Referring to FIGS. 6-7, the cuvette assembly 110 includes four separate cuvettes, each of which includes an optical chamber 112 and a liquid-input chamber 114. The internal and external walls of the lower portion 113 of the main body of the cuvette assembly 110 define the optical chamber 112. For example, the first optical chamber 112 is partially defined by the side external wall, an internal wall, and a bottom wall of the lower portion 113, as well as the entry and exit windows 116, 118. The associated liquid-input chamber 114 is partially defined by a side external wall, an internal wall, and a pair of front and back external walls on the upper portion 115 of the main body of the cuvette assembly 110.

Each of the four entry windows 116 is a part of an entry window assembly 117 that is attached to the lower portion 113 of the main body of the cuvette assembly 110. Similarly, each of the four exit windows 118 is part of an exit window assembly 119 that is attached to the lower portion of the main body opposite the entry window assembly 117. In other words, the present invention contemplates a single unitary optical structure that provides the transmission of the input beam 21 into all four respective optical chambers 112, and a single unitary optical structure that provides for the exit of the forward-scatter signals from the respective optical chambers 112. The lower portion 113 of the main body includes structural recesses that mate with the corresponding structures on the window assemblies 117, 119 for registering them in a proper orientation during assembly of the cuvette assembly 110.

An intermediate partition 130 within the cuvette assembly 110 separates the lower portion 113 defining the four optical chambers 112 from the upper portion 115 defining the liquid-input chambers 114. The intermediate partition 130, which is shown as being part of the lower portion 113 (although it could be part of the upper portion 115), includes four separate groups of openings that permit the flow of liquid from the liquid-input chamber 114 into the associated optical chamber 112. The openings can be a variety of shapes that permit the flow of the liquid. As shown, the openings progressively get longer moving from the entry window 116 to the exit window 118 because the shape of the optical chamber 112 increases in area in the same direction. Additionally, the filter 132 rests upon the intermediate partition 130, such that the same filter 132 is used for each of the four regions. When the same filter 132 is used for all four regions, the interior walls of the upper portion 115 must provide adequate pressure at the filter 132 to prevent crossing fluid flows through the filter 132 between adjacent liquid-input chambers 112. In a further alternative, no filter 132 is present because the intermediate partition 130 includes adequate sized openings to provide the necessary filtering of the liquid sample, or because the liquid samples are pre-filtered before entering each liquid-input chamber 114.

To provide the initial introduction of the liquid samples into the cuvette assembly 110, the upper structure 138, which is attached to the upper portion 115 of the main body of the cuvette assembly 110, includes four openings 140 corresponding to the four liquid-input chambers 114. Four sliding mechanisms 142 are located within four corresponding grooves 144 on the upper structure 138 and are initially placed in an opened position such that the openings 140 are initially accessible to the user for introducing the liquid samples. Each of the sliding mechanisms 142 includes a pair of projections 148 that engage corresponding side channels at the edges of each of the corresponding grooves 144 to permit the sliding action. Within each groove 144, there is a latching ramp 146 over which the sliding mechanism 142 is moved when transitioning to its closed position. A corresponding latch 147 (FIG. 4) on the underside of the sliding mechanism 142 moves over the latching ramp 146 and creates a locking mechanism when the sliding mechanism 142 has been fully moved to the closed position. The upper structure 138 of the cuvette assembly 110 also includes a gripping handle 150 that permits the user to easily grasp the cuvette assembly 110 during transport to and from the platform 210 within the instrument 10 that incorporates the light source 20 and the sensor 22.

To help seal the cuvette assembly 110 after the liquid samples have been placed within the respective liquid-input chambers 114, the periphery of the sliding mechanism 142 adjacent to the opening 140 can be configured to tightly mate with the walls defining the groove 144 (or undercut channels within the groove 144) to inhibit any leakage around the opening 140 in the upper structure 138. Alternatively, a resilient plug-like structure can be located on the underside of the sliding mechanism 142 that fits within the opening 142 create a seal and inhibit leakage. Or, a gasket can be provided around the opening 140 to provide a sealing effect on the underside of the sliding mechanism 142. The cuvette assemblies 110 provide well sealed containment of the samples that reduces evaporation loss.

The upper portion 115 and the lower portion 113 of the main body of the cuvette assembly 110 can be attached to each other through various techniques, such as ultrasonic welding, thermal welding, with adhesive, or through interfering snap-fit connections. Similarly, the upper structure 138 can be attached to the upper portion 115 of the main body through similar techniques. And, the window assemblies 117, 119 can be attached to the lower portion 113 through the same attachment techniques. The width dimension of the overall cuvette assembly 110 across the four cuvettes is roughly 4 cm. The length dimension of the overall cuvette assembly 110 (i.e., parallel to the input beam) is approximately 2 cm. The height dimension of the overall cuvette assembly 110 is approximately 2 cm, such that each of the liquid input chambers 114 is approximately 1 cm in height and each of the optical chambers 112 is approximately 1 cm in height (although the optical chambers 112 have a varying height along the length direction due to their conical shape). In some embodiments, each optical chamber 112 is designed to contain approximately 1.2 to 1.5 cubic centimeters (i.e., approximately 1.2 to 1.5 ml) of a fluid sample. Each liquid-input chamber 114 is designed to hold slightly more of the liquid sample (e.g., 1.7 to 2.5 ml), which is then fed into the corresponding optical chamber 112.

Because each of the cuvette assemblies 110 may be used for different applications, the cuvette assembly 110 may use barcodes or RFID tags to identify the type of test supported by the particular cuvette assembly 110, as well as other measurement data to be taken. The instrument 10 that includes the light source 20 preferably reads the RFID or barcode, and selects the software program with the memory device 60 to run the appropriate optical measurement tests on the cuvette assembly 110. Accordingly, the cuvette assembly 110 preferably includes an identification label 170, which may include barcodes and/or quick response codes ("QR-code") that provide the necessary coded information for the cuvette assembly 110. Other codes can be used as well. Specifically, when bacteria is a particle being checked within the liquid sample, one of the codes on the label 170 may provide the protocol for the test (e.g., temperature profile over duration of test, frequency of the optical measurements, duration of test, etc.), and the processor 50 executes instructions from the memory 60 (FIG. 5) corresponding to the test protocol. Another one of the codes may be associated with information on the patient(s) from whom the liquid samples were taken, which may include some level of encryption to ensure that patient data is kept confidential. Another code may provide a quality-assurance check of the part number or the serial number for the cuvette assembly 110 to ensure that the cuvette assembly 110 is an authentic and genuine part, such that improper cuvettes are not tested. The code for the quality-assurance check may also prevent a cuvette assembly 110 from being tested a second time (perhaps after some type of cleaning) if it is intended for only single use. Again, the instrument 110 preferably includes a device to read the codes associated with the label 170 (such as an image sensor, a barcode reader/sensor, or a QR-code reader/sensor). Alternatively, the codes on the label 170 can be scanned as the assemblies 110 are placed into the platform 210 (FIG. 8) such that the necessary information is obtained prior to the door 12 being closed.

The cuvette assembly 110 also includes a vent 180 (FIG. 7) that extends from the optical chamber 112 into the upper portion 115 of the main body the cuvette assembly 110. The vent 180 includes a chimney-like portion that extends upwardly from the intermediate partition 130. The chimney-like portion is then received in a channel in the upper portion 115, which extends to an opening 182 leading into the liquid-input chamber 114 just below the upper structure 138 that defines the upper boundary of the liquid-input chamber 114. Accordingly, the gas (e.g., air) that is initially present in the optical chamber 112 can be readily displaced as the optical chamber 112 receives the filtered liquid sample from the liquid-input chamber 114 (via the filter 132). The vent 180 can also lead to the external environment on the outside of the cuvette assembly 110.

Figure 8:
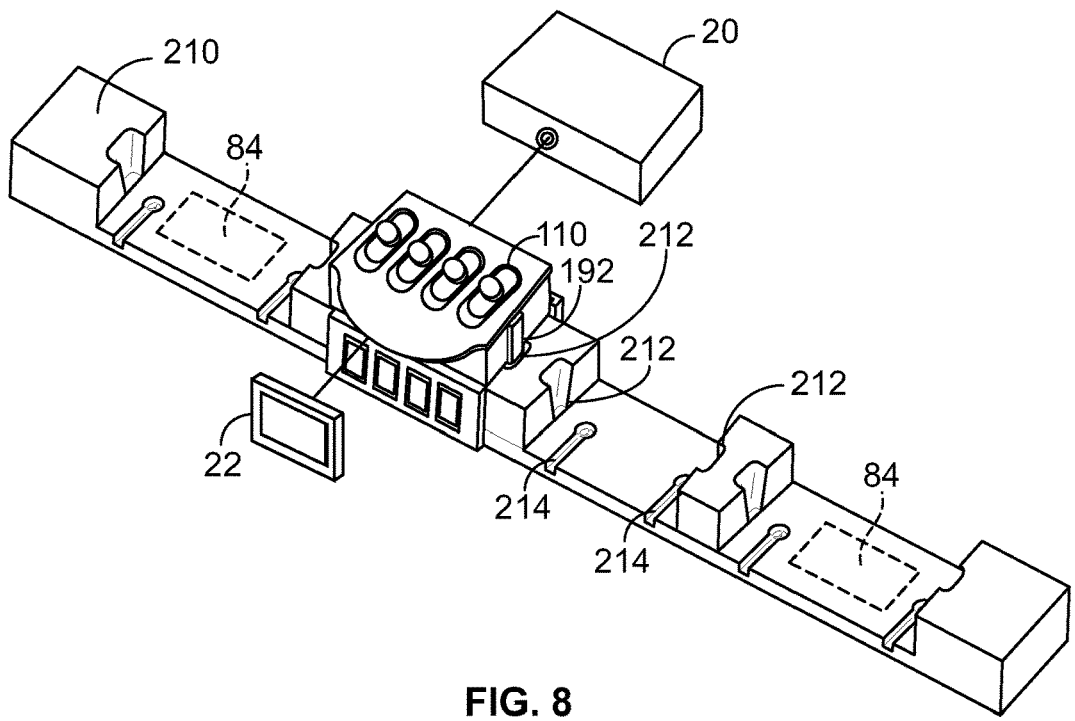
FIG. 8 illustrates the cuvette assembly of FIGS. 2, 6 and 7 registered on a platform or tray (typically heated) that is movable from the open position in which the instrument's door is opened for loading to the closed position in which the instrument's door is closed for sample testing within the optical measurement instrument of FIGS. 1A and 1B

FIG. 8 illustrates how the cuvettes assemblies 110 are registered with the optical measurement instrument 10 within a registration platform or tray 210, which is a part of the instrument 10. Each of the cuvettes assemblies 110 includes side registration features 192 that undergo a sliding engagement within corresponding vertical grooves 212 on pillars associated with the registration platform 210. Additionally, lower registration features 194 (FIG. 6) can slide within horizontal grooves 214 on an upper surface of the registration platform 210. The horizontal grooves 214 terminate in openings that receive the lower registration features 194 (illustrated as projections) on the cuvette assembly 110. Finally, the distance between the lower segments of the front and back walls of the cuvette assembly 110 corresponds to the width of the registration platform 210 such that cuvette assembly 110 becomes nestled between adjacent pillars with the front and back walls overlying the front and back edges of the registration platform 210.

As can be seen best in FIGS. 6-7, the lower surface of the lower portion 113 of the cuvette assembly 110, which includes the lower registration features 194, is at angle relative to the upper structure 138 of the cuvette assembly 110 and to the input beam from the light source 20 due to the conical geometry of the optical chamber 112. Accordingly, the upper surface of the registration platform 210 is angled in an opposing manner that allows the input beam to be generally horizontal (and generally parallel to the upper structure 138 of the cuvette assembly 110) when the cuvette assembly 110 is placed on the registration platform 210. It should be noted, however, that the cuvette assembly 110 can be properly registered on the registration platform 210 with less than these three distinct registration features illustrated in FIG. 8.

Once the cuvette assembly 110 is nestled properly on the registration platform 210, the door motor 16 is actuated, causing the now-loaded registration platform 210 to be pulled into the instrument 10 and the door 12 to be closed. The light source 20 can then sequentially transmit the input beam through each of the four optical chambers 112 of each cuvette assembly 110 and the forward-scatter signal associated with the particles within each of the liquid samples can be sequentially received by the sensor 22. The light source 20 and the sensor 22 on the optical bench 18 are controllably indexed between positions to receive optical measurements taken in adjacent optical chambers 112. As can be seen in FIG. 8, each platform 210 is capable of receiving four cuvette assemblies 110, such that optical measurements can be taken from sixteen different liquid samples within the four cuvette assemblies 110 nestled on the registration platform 210. Of course, the present invention contemplates an instrument 10 that uses more or less than four cuvettes assemblies 110.

According to this first embodiment, the instrument 10 has the optical beam 21 along a line from the laser 20 (or other light source such as an LED or lamp) and a light/image sensor 22 such as a camera, imager, calorimeter, thermopile, or solid-state detector array. The liquid samples are contained in the optical chambers 112 of the cuvette assemblies 110 between the light source 20 and the sensor 22 with at least one window so that light can transmit through the sample to the sensor 22. The light source 20 producing the optical beam 21 and the sensor 22 are rigidly mounted to a mechanical optical bench 18 (or plate), and the bench 18 is preferably mounted on rails or other mechanical structures for translational motion (or rotational motion) via a stepper motor 24 (or a motorized threaded stage that moves the bench, or a flexible motor-driven belt) so that it can be moved precisely relative to the sample in the cuvette 110 so that multiple samples can be optically measured. Additionally, the bench 18 could be translated to a diagnostic station 90 with no sample present (far right position of the optical bench 18 in FIG. 4) so that it can undergo self-testing or diagnostics in which the sensor 22 confirms performance of the light source 20, and the light source 20 confirms performance of the sensor 22, including provisions of a reticle or other optical devices that can be sensed to confirm alignment or optical power levels.

The sample-containing cuvettes 110 and the optical components are contained in an enclosure within the instrument 10 that excludes most ambient light, which might impact the measurement by the sensor. Alternatively, some portion of the sample cuvette or container could form a light-tight cover on the instrument, as described below in FIG. 9.

In this first embodiment, the sample-containing cuvettes 110 are disposable containers set on the platform 210 or tray or rail, which preferably includes the heating system 84, such as electrical resistance heaters or pelletier devices and the thermal sensors 82, such as common thermocouples. The heating system 84 and thermal sensors 82 form part of the incubation system that provide for appropriate temperature controls during operation of the instrument 10. The electronic control system in FIG. 5 provides for the thermostatic control of the temperature of the platform 210 and, thus, the contained liquid samples can be warmed or cooled (for example, through fans pulling in cooler air to the enclosure) to a set temperature to influence biological or chemical behavior of the liquid samples. Alternatively, the samples (and cuvettes 110) could be illuminated by optical or infrared (IR) light sources for heating, and the temperature can be measured or implied by direct or remote sensors.

Furthermore, the platform 210 may be equipped with a vibration-producing mechanism to help agitate the samples in the cuvettes 110. For example, a vibration motor can be coupled to the platform and 210 operated between cycles of the laser operation.

Figure 9:
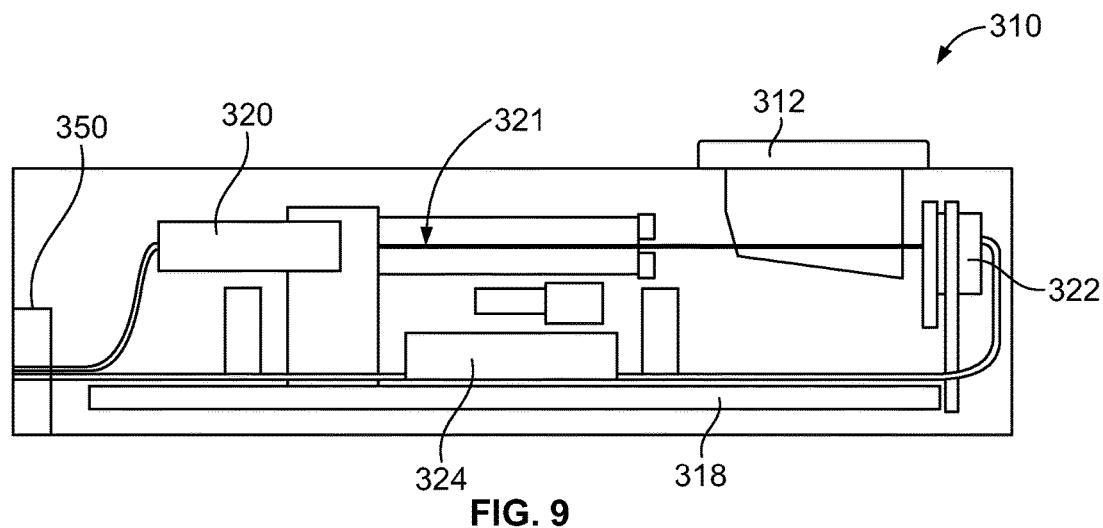
FIG. 9 illustrates an alternative optical-measuring instrument that is capable of incubating fluid samples in which the cuvettes form part of the light-tight closure of the optical-measuring instrument.

FIG. 9 illustrates an alternative optical-measuring instrument 310 that is capable of incubating fluid samples in cuvettes 312. However, unlike the previous embodiments, the cuvettes 312 form part of the light-tight closure of the optical-measuring instrument 310. In particular, the cuvettes 312 have an upper flange that rest on the exterior surface of the instrument 310. The exterior surface includes openings sized to receive the cuvettes in a certain notation, such that the upper flange rests against the exterior surface. When placed within the optical measuring instrument 310, the entrance and exit windows of the cuvettes are properly aligned with an input laser beam 321 from the laser 320 and the sensor 322 so as to provide proper registration for measuring the forward-scatter signal associated with the liquid sample. As in previous embodiments, the laser 320 and the sensor 322 would be mounted on an optical bench 318 that translates within the enclosure of the optical measuring instrument 310 by use of a stepper motor 324. As with the previous embodiments, the functions of the instrument 310 would be controlled by one or more processors 350. The optical bench 318 may include other optical components, such as lenses and apertures, to properly develop the laser beam 321 prior to transmission through the liquid sample in the cuvettes 312. The cuvettes 312 may have internal structures similar to those of the cuvette assemblies 110 in FIGS. 6-7.

Figure 10:
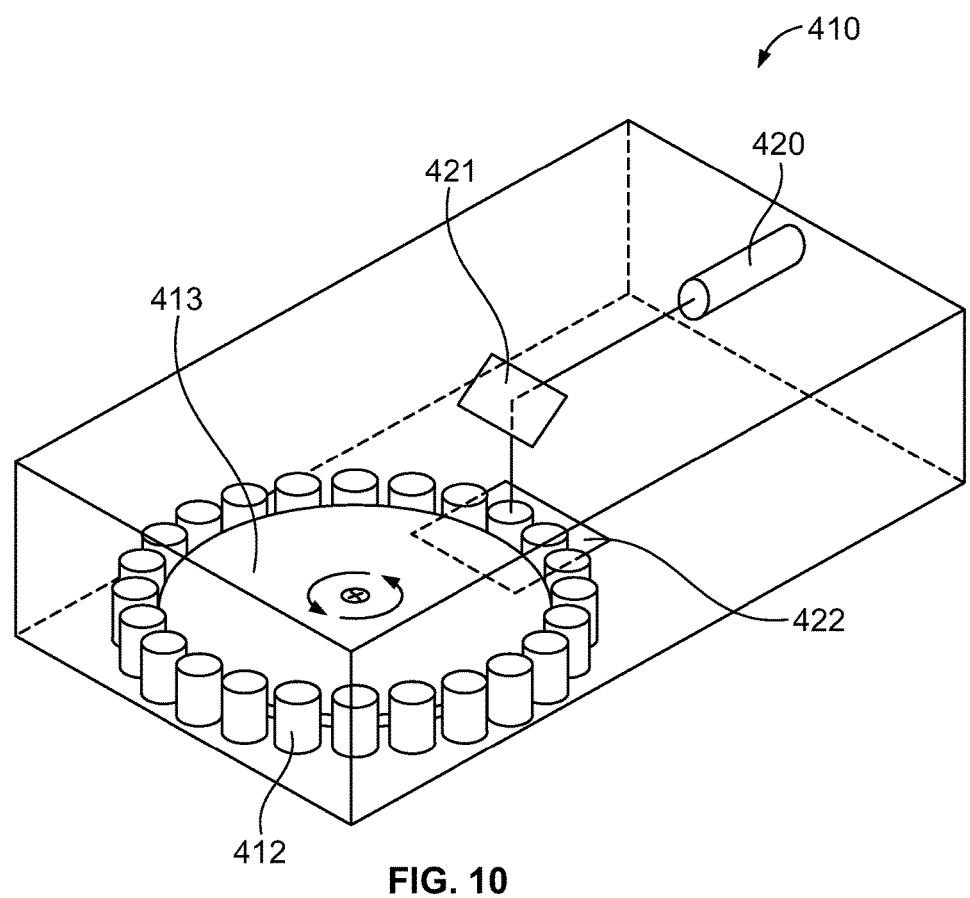
FIG. 10 is an isometric view of optical-measuring instrument with fixed optical elements and multiple cuvettes that are rotated on a rotatable platform into the light beam for measuring optical characteristics of multiple samples.

FIG. 10 illustrates another embodiment of an optical measuring instrument 410 that has one or more input beam lines that are fixed, which is different from the previous embodiments in which the beam lines are translated via the moving optical bench, which includes the laser and sensor. In the embodiment of FIG. 10, multiple sample chambers 412 (e.g., cuvettes) are held by a translatable or rotatable platform 413 that moves each sample into the light path within the optical measuring instrument 410. The light is developed by a light source, such as a laser 420 and may reflect off a turning mirror 421 before being transmitted through the fluid sample within the sample chamber 412. A sensor 422 receives the optical signal (e.g., a forward-scatter signal), which is then processed/analyzed to determine the presence and/or growth of bacteria over a period of time. The optical measuring instrument 410 may incorporate conductive heating and cooling, or radiant heating from an optical or infrared source for control of the temperature of the fluid samples, thereby providing the proper incubation.

In yet another embodiment of the instruments 10, 310, 410, the light source and sensor are fixed, and the multiple sample chambers are fixed. However, optical elements such as mirrors or prisms on electro-mechanical actuators are used to move the light beam from measurement chamber to measurement chamber within each sample. Hence, the electro-mechanical actuators and possibly motors are used to move the light beam, while the light source, the sensor(s), and the multiple sample chambers are fixed. In yet a further embodiment, there is a fixed sensor associated with each cuvette/sample position (e.g., such that the instrument has 16 individual sensors) and only the light source translates.

In one mode of operation of the optical measuring system, the fluid samples in the cuvettes or fluid chambers may be developed from a single sample (e.g., from a single patient) constituted from one or multiple liquids and/or dry materials that are combined and mixed. Each of the fluid chambers could be pre-loaded with a chemoeffector including a drug, antimicrobial agent, nutrient, chemical tag or colorant. Each measurement chamber is then sequentially measured with one or more optical beam lines, or by moving the beam lines around the sample assembly. If each individual measurement chamber includes a different chemoeffector (e.g., different dosage of an antibiotic), then the effect of the separate chemoeffector can be monitored over time for a single fluid sample. Thus, each of the optical measurement instruments in FIGS. 1-10 can be used to determine the effects of a chemoeffector (a drug, antimicrobial agent, nutrient, chemical tag or colorant) on a single sample if the cuvette (such as cuvettes assembly 110) is loaded with a sample from a single patient, but the chambers includes different chemoeffectors (or each cuvette assembly 110 is designed to test a single chemoeffector four times for accuracy/repeatability). Thus, in the instrument 10 of FIGS. 1-5, a single patient's sample could be tested against multiple chemoffectors. The codes on the label 170 on the cuvette assembly 110 may identify which chemoeffector is being tested within the respective assembly 110.

Regarding the operation of the instrument 10, one sample of test data from each fluid sample can be developed and recorded locally in the memory 60 within about 10 seconds. The laser 20 beam is transmitted through the sample contained between two windows, and into the sensor 22. The sensor 22 captures the scattered light across its surface and measures the distribution of light intensity as a forward scatter signal, which is them stored locally for a period of time, before being downloaded (on a periodic basis) to a larger memory device (e.g., the Measurements Database 620 in the network 600 in FIG. 19) that is linked to the instrument 10. Similarly, the intensity of the laser beam on the sensor 22 can be measured in a location where there is no sample present, and again measured through the sample to determine the amount of power reduction that is attributable to absorption or reflectance of the enclosed sample, and the difference in these two values can be used to calculate optical density for the sample. As such, the instrument 10 can measure optical density of the fluid samples, which provides another piece of data that can be used for determining the bacterial concentration and its growth over a period of time. The optical bench 18 then translates to the position corresponding to the next sample. Accordingly, if sixteen samples are present (4 cuvette assemblies 110, each with 4 sample chambers), then the all sixteen samples can be completed in approximately 2-3 minutes. As such, the laser 20 and the sensor 22 continuously cycle through the fluid samples and measure a forward-scatter data point for each of the sixteen samples in about 2-3 minutes. For example, in a 2-hour test period, twenty or more multiple scatter signals for each of fluid samples can be taken.

The instrument 10 measures bacteria and other organisms generally in the range for 0.1 to 10 microns with a measurement repeatability of 10%. The instrument 10 can measure a low concentration of $1\times10^4$ cfu/ml (based on *E-coli* in filtered saline) and deliver continuous measurements showing growth beyond $1\times10^9$ cfu/ml. The instrument 10 can be loaded with factory-set calibration factors for approximate quantification of common organisms. Further, the user can load custom calibration factors with specific test protocols for use with less common organisms or processes.

Considering that the particles in the fluid (especially bacteria) may be in motion, it is possible that large clusters may affect the forward-scatter signal on any given test sample. Accordingly, in one preferred embodiment, multiple consecutive test data points for each fluid sample are averaged to avoid having a single forward-scatter signal with a large cluster of particles or a single forward-scatter signal corresponding to only a few particles affect the overall test results. In one example, five consecutive forward-scatter signal test data points are averaged under a rolling-average method to develop a single average signal. Thus, as a new data point is taken for each sample, it is used with the previous four data points to develop a new average. More or less data points than five can be used for this rolling average. Further, the computation methodology may use various algorithms to remove the high and low signals (or certain ultra-high or ultra-low signals) before taking the average. Or, the computation methodology can be as simple as choosing the mathematical median of a data set. Ultimately, the forward-scatter signals from the instrument 10 will produce a bacterial-growth curve having a certain slope over a period of time at an appropriate incubation temperature.

Generally, growth curves are numerically filtered and analyzed for determination of initial concentration, growth percentage for a predefined period of time, and changes in the growth rate. Determination of bacterial absence or bacterial presence above a predefined threshold is based on a combination of those parameters with thresholds that are characteristic for bacterial growth and salts crystallization/dissolving kinetics. In one basic example, if the slope is above a predetermined value, the patient's sample is infected. Alternatively, it could be that the slope that indicates the presence of an infection may be different for different periods of time (e.g., $Slope_{infection} > X$ within T=0 to 30 minutes; $Slope_{infection} > 1.5X$ within T=30 to 60 minutes; etc.)

Particles with a refractive index different from the surrounding medium will scatter light, and the resultant scattering intensity/angular distribution depends on the particle size, refractive index and shape. In situations in which the input light is scattered more than one time before exiting the sample (known as multiple scattering), the scattering also depends on the concentration of particles. Typically, bacteria have a refractive index close to that of water, indicating they are relatively transparent and scatter a small fraction of the incident beam, predominantly in the forward direction. With the optical design within the instrument 10, it is possible to look at scattering angles down to about 2° without having the incident input beam or other noise signals (e.g., the scattering from the cuvette windows) interfere with light scattered by bacteria. By simultaneous measurement of the forward scattering and optical density, measurements could be extended down to $10^{-5}$, allowing accurate measurement of concentrations as low as $10^3$ CFU/mL.

Optical density measurements are intended to determine sample concentrations that are not accurate, as the size of the scattering particles greatly affects the resulting optical density. A similar optical density is obtained for samples with a few large size bacteria in comparison with a higher concentration of small size bacterial samples. Moreover, additional calibration of the optical density to concentration does not render more accurate results, since the size changes during the bacterial growth process.

Bu use of the Mie scattering model for spherical particles and the T-matrix method of light scattering, combined with Monte-Carlo ray tracing calculation that takes into account multiple scattering, it is possible to evaluate the number of bacteria and their size from the measurement of the optical density and the scattered light angular distribution.

The results are nearly independent of the specific particle shape and loosely depend on the size dispersion of bacteria, resulting in a small constant shift of the mean size. Thus, both bacterial concentration and size are evaluated from the measured parameters by a first principle model without any free parameters, except the bacteria refractive index, that is measured by calibration for each of the bacteria species. In short, the instrument 10 can be used to detect forward scatter signals corresponding to scattering intensity and angular distribution (e.g., for angles less than 5°, such as angles down to about 2°) and also the optical density of the fluid samples, which can then be evaluated to determine the number of bacteria and their sizes (and changes to the number of bacteria and to their sizes over a period of time).

FIG. 11 illustrates a screen shot 450 from the display device that would be coupled to the instrument 10 via the USB communication port 30. The bacterial growth curves for seven different patients' urine samples 451-457 are illustrated. The curves are based on both forward-laser scattering and optical density testing, and correlated to estimated organism concentrations as discussed above. The samples 451, 456, and 457 show bacterial growth, which is an indication of infection. The sample 456 has only a slight slope, but enough to indicate that the particles (bacteria) are increasing. On the other hand, the samples 451 and 457 have much steeper slopes. On the other hand, samples 452 and 453 have no substantially slope, which suggests no bacterial growth. The sample 454 shows a little potential growth through its slight slope. But because the sample 454 started high (suggesting a highly turbid sample), there may be a recommendation for further testing as there may be some bacterial growth hidden in the cloudiness. The sample 455 is a "rapid riser," which is a sample with high concentration of phosphate salts that precipitate out in a cloud when warmed up, which causes the very sharp rise in particle concentration. This sample 455 represents a rare occurrence (e.g., <5% of all cases) in testing using the device 10, and would require further testing. In short, the patients corresponding to samples 451, 456, and 457 have a clear infection, that can be identified and treated within 2-3 hours of testing. For a sample like the patient sample 451, the system can set off an audio and/or visual alarm (e.g., blinking sample, flashing notification, scrolling banner across the bottom of the screen) once the slope reaches a certain level, indicating a very high probability of an infection. (e.g., after 30 or 40 minutes)

FIG. 11 also shows raw-data region 460, which allows the operator to review the actual test data for any given sample. Keep in mind that the screen shot 450 for the display device is presenting information to the operator who is monitoring five or ten instruments 10 that are in operation. Thus, the operator can access the raw data for various tests and develop graphs of various samples by clicking on the raw data samples within the raw-data region 460. And the graphs can be plotted in real time on the display device.

Also shown on FIG. 11 are several possible features to facilitate use, including software icons for delivering various data screens to the user for loading a new sample (shown as a "New Cuvette" button on FIG. 11, for archiving data on a separate data storage media (shown as a "data disk" icon), for searching for particular sample results (shown as a "magnifying glass" icon), for pausing instrument operation (shown as a "play arrow" icon), and for opening the instrument door to load or unload samples (shown as a "Eject Arrow" icon).

Another icon shown in FIG. 11 is the "Biohazard" button, which is programmed to analyze a selection of samples to plot out organism growth as a function of the concentration of a particular chemoeffector or other value that has been linked to the samples. The screen on FIG. 11 has other icons that can be used to control and monitor the instrument 10, sort, analyze and visualize the loaded and collected data and results, and operate the instrument 10. Other icons can be added or deleted as the needs of the user are refined or evolve.

FIG. 12 illustrates a screen shot 470 from the display device that would be coupled to the instrument 10 via the USB communication port 30. The bacterial growth curves for eight samples 471-478 derived from the same bacteria-infected sample is illustrated, which in this case is used for anti-microbial susceptibility testing (AST). The difference in the samples is the different levels of the antibiotics that have been applied to the sample. From sample 478, no RX treatment of the staph infection has caused a large increase in the bacterial population. And even for the lower levels of the antibiotics shown in lines 475, 476, 477, there is still some bacterial growth. However, once the antibiotic level reaches 0.125 μg/ml, the antibiotic has killed the bacterial colony as shown in sample line 474. Additionally, higher antibiotic levels, as shown in samples 471-473 yields no greater effect that sample line 474. Accordingly, the instrument 10 can be used to determine the correct concentration of a certain antibiotic that should effectively eradicate a bacterial colony. It should be noted that the time scale on the graph on the screen-shot 470 illustrates that the instrument 10 can provide automated measurements for hours or days.

Like FIG. 11, FIG. 12 also shows a raw data field 480 for the AST that identifies the antibiotics being tested along with the bacteria types. The operator can scroll through the data and locate tests that he or she wants to review or have graphed.

The system and method associated with FIGS. 1-12 have various uses and applications. For example, in the area of research, it can be used for (i) microbial concentration and grow analyses, (ii) quantification of antimicrobial, antibiotics, and environmental effects, and (iii) antibiotic drug development and clinical trial enrollment. In the area of hygiene and safety, it can be used for (iv) antimicrobial and antibiotics quality assurance testing, (v) process and potable water testing, and (vi) surface, wipe, and swab microbial testing. In the area of clinical microbiology for humans and animals, it can be used for (vii) rapid detection and quantification of infection, (viii) rapid antibiotic susceptibility testing (AST), (ix) drug-testing and measurement, and (x) antibiotic sensitivity testing for quality control.

The present invention associated with FIGS. 1-12 also contemplates the identification (or partial identification) of the type of bacteria that is present in fluid sample. For example, if a certain type of fluid is known to have a limited number of types of bacteria, one type of bacteria may be known to grow at a fast rate at a certain incubation temperature relative to the other bacteria, leading to a higher slope on the growth curves. One type of bacteria may be known to grow at a slower rate at a certain incubation temperature relative to the other bacteria, leading to a lower slope on the growth curves. Or a group of bacteria may be known to have certain growth curves, leading to the partial identification by eliminating the other types of bacteria that may be possibly present in the fluid sample. Using multiple instruments 10 with the same set of fluid samples but at different incubation temperatures (e.g., the same sixteen samples in three instruments 10 at 38° C., 40° C., and 42° C.) can result in different bacterial-growth curves, which identify one type of bacteria relative another (or at least a species of bacteria). Further, if one bacteria (or a species of bacteria) are known to die above a certain temperature, then after the samples have been tested, the instrument 10 can ramp-up the temperature to see if the growth curve flattens for any sample, indicating that the sample may be infected by the bacteria that is known to die above the operating temperature.

In a further example, complex UTI cases in humans are known to have both Gram Positive bacteria and Gram Negative bacteria. Crystal Violet is a dye that adheres to the rough surface of Gram Positive bacteria and, in the process, causes the pores on the surface to become "clogged" so as to kill the Gram Positive bacteria. Therefore, inclusion of Crystal Violet in one chamber of the cuvette assembly 110 while other chambers in the cuvette assembly 110 lack it permits identification of the UTI infection type. If the bacteria growth curve continues similarly in both chambers, then the patient's sample is likely infected by only a Gram Negative bacteria. On the other hand, if the bacteria growth curve in the chamber having Crystal Violet has a substantially smaller slope, then the infection likely includes a Gram Positive bacteria. As such, at least a partial identification of the bacteria has been achieved. In this case, the chemoeffector is an inert chemistry (Crystal Violet) that impacts the growth behavior of the organisms, and by comparison to a control, some identification information for the bacteria can be obtained.

Figure 13:
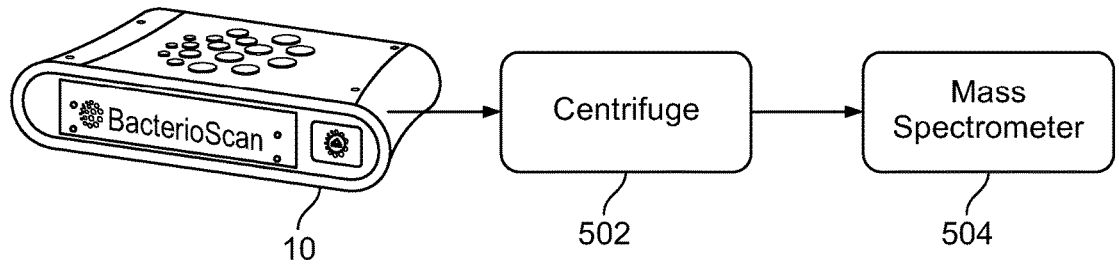
FIG. 13 illustrates a system for detecting the presence of bacteria in a fluid sample, and then determining the type of bacteria that is present in the fluid sample.
Figure 14:
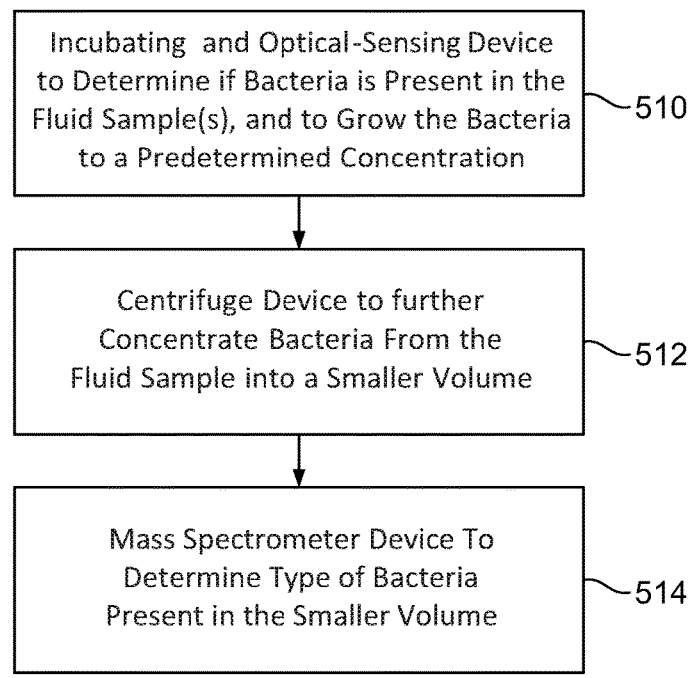
FIG. 14 illustrates a flow diagram to be used with the devices in FIG. 13.

Regarding the identification of the bacteria, FIGS. 13 and 14 illustrate another aspect of the present invention using additional devices and methods to identify which type of bacteria is present within the fluid sample. In this aspect of the invention, as shown schematically in FIG. 13, the optical-sensing instrument 10 is first used. Next, the system may involve the actions of a centrifuge 502 on a fluid sample from the optical-sensing instrument 10. And finally, a mass spectrometer 504 is used on the fluid sample.

In FIG. 14, the process using the devices of FIG. 13 on a fluid sample (for example, urine samples) is illustrated. Initially, at step 510, the fluid samples from a variety of patients are placed into an incubating and optical sensing instrument, such as the instrument 10 shown in FIG. 1. For example, fluid samples from sixteen patients can be placed in the four cuvettes 110 of FIG. 2, which are then placed within the incubating optical sensing instrument 10 in FIG. 1. If one or more of the sixteen fluid samples is detected as having bacteria, the incubation process continues until a desired concentration of bacteria is present within the fluid sample (for example, a concentration of $1 \times 10^6$ cfu/ml). In response to the forward-scatter signals for the sample as measured by the device of FIG. 1 indicating the desired concentration, the corresponding cuvette with the target fluid sample is then removed from the incubating and optical sensing instrument 10, and the fluid sample with the desired concentration of bacteria is then removed from the corresponding chamber of the cuvette by, for example, a pipette. At step 512, the fluid sample with the desired concentration of bacteria from the cuvette is then placed into a centrifuge device to further concentrate the bacteria into a smaller volume (e.g., $1 \times 10^9$ cfu/ml), which permits the type of bacteria to be identified through a mass spectrometer. A washing process (perhaps repeated) with purified water may be used in conjunction with the centrifuging process to better concentrate the bacteria. After the centrifuging process, at step 514, the concentrated bacteria are placed into a mass-spectrometry microbial identification device that can be used to identify the type of bacteria that was within the original fluid sample (for example, a urine sample from a particular patient). This third device may be a Biotyper Matrix Assisted Laser Desorption Ionization-Time of Flight Mass Spectrometer (MALDI-TOF) from the Bruker Corporation, or a Vitek® MS device from bioMérieux SA. Other known devices that use a mass spectrometer to identify the type of bacteria can be used as well. Accordingly, the optical sensing instrument 10 is not only used to identify the presence of bacteria, but it is then used to incubate the bacteria to achieve a certain concentration of bacteria that can then be used to conduct a bacteria-identification process.

Figure 15:
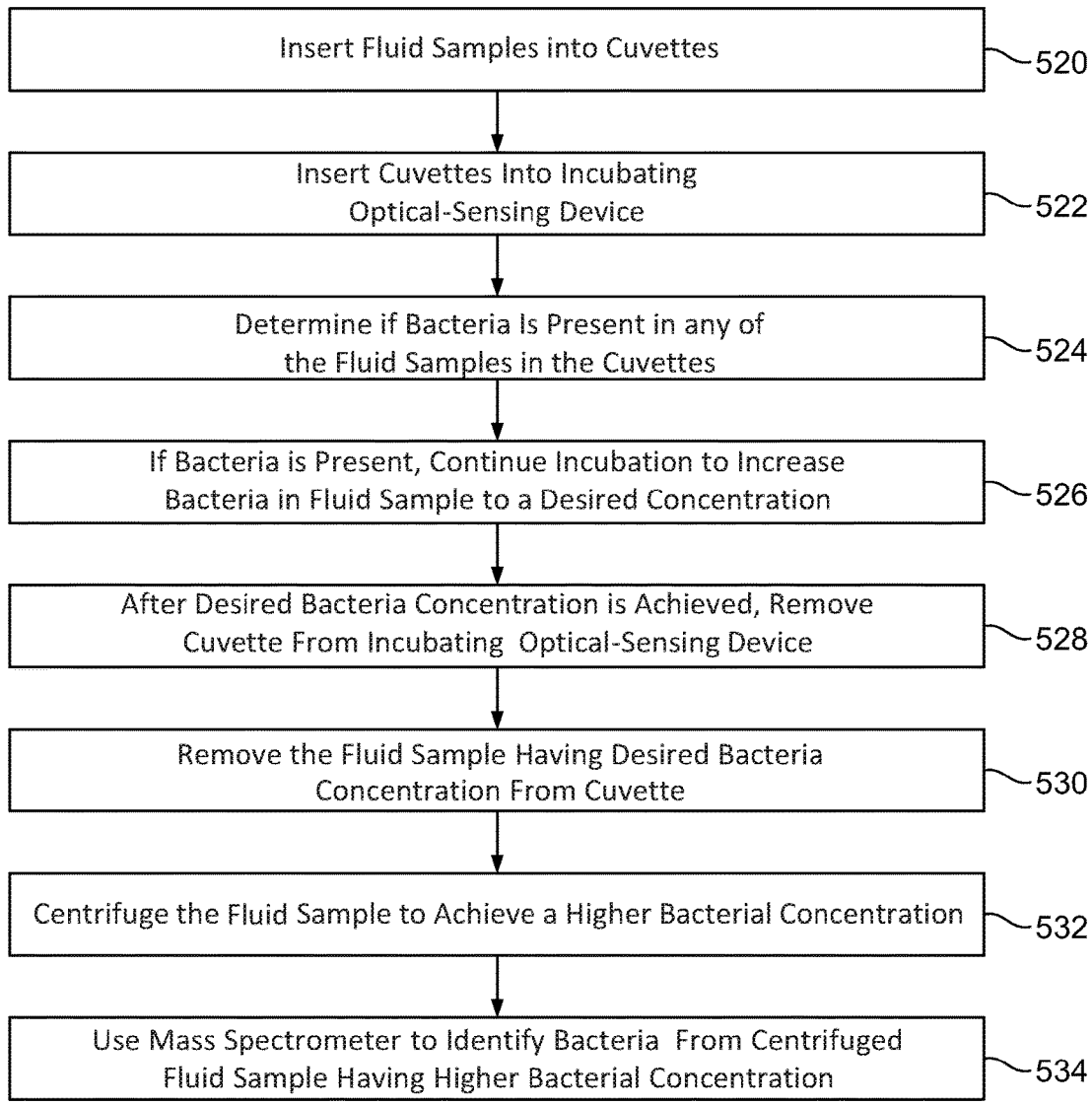
FIG. 15 illustrates a flow diagram involving the process that is used to detect the presence of bacteria in a fluid sample, and then determine the type of bacteria that is present.

FIG. 15 provides a more detailed process flow for identifying the type of bacteria within a plurality of different fluid samples using the cuvettes and incubating and optical measurement device 10. In particular, the fluid samples are loaded into the cuvettes 110 at step 520. The cuvettes 110 are then loaded into the optical sensing instrument, such as instrument 10, in step 522. The optical sensing instrument determines if any of the fluid samples have bacteria present at step 524. If bacteria are detected, the incubation continues for the purpose of increasing the bacteria concentration to a predetermined level at step 526. After the desired bacteria concentration is achieved, the cuvettes 110 are removed from the instrument 10 at step 528. The fluid sample(s) having the desired bacteria concentration is achieved is removed from the cuvette 110 (possibly by use of a pipette) at step 530, and the fluid is centrifuged at step 532 to achieve a fluid with a higher bacteria concentration that is needed for mass spectroscopy. It should be noted that, in some instances, the centrifuge may not be needed as the bacteria concentration from the prolonged incubation should be high enough for identification via mass spectroscopy. Finally, at step 534, the fluid with the higher bacteria concentration from the centrifuge is placed in a mass spectrometer and the bacteria is then identified.

Example 1

The following information provides one exemplary test process in accordance to FIGS. 13-15, which is related to the use of e. coli ((ATCC25922):

A freshly grown e. coli (ATCC25922) colony is diluted and placed in a Luria Broth (LB) to achieve a $1 \times 10^4$ CFU/ml concentration level. The $1 \times 10^4$ CFU/ml concentration level is the minimum bacteria concentration for indicating a urinary tract infection.

Three ~2 mL aliquots are loaded into three chambers of 4-chamber multi-cuvette (FIG. 2), and the fourth chamber was used for LB control to confirm sterility.

Concentration curves are obtained on ~2 minute intervals in a BacterioScan 216R instrument (FIG. 1), with samples heated to 37° C.

When the sample concentration reaches $10^5$, $10^6$, $10^7$ & $10^8$ cfu/ml as detected by the BacterioScan 216R, (i) an aliquot of 1 μl is loaded onto MALDI-TOF device ("wet target") and (ii) an aliquot of 1 ml is processed via a centrifuging/washing process into a pellet ("dry target") having a higher bacteria concentration, which is then loaded into a MALDI-TOF device.

To confirm the sample concentrations, a 10 uL streak culture is plated on 5% defibrinated sheep blood agar plates, incubated, and colonies are counted.

A static culture (e. coli at $1 \times 10^4$ CFU/ml in 25 mL of LB) is created and incubated at 37° C., and processed as above (dry & wet target for MALDI, with 10 ul plated on blood agar).

The entire experiment is performed twice—Day 1 & Day 2.

Day 1 dry samples are centrifuged for 2 minutes each.

Day 2 dry samples are centrifuged for 5 minutes each.

Regarding the results, only the "Dry target" method was successful in identifying the type of bacteria via the MALDI. The "Wet target" method did not achieve a high enough concentration of bacteria before being placed in the MALDI to permit identification of the bacteria. However, the present invention contemplates that the "Wet target" method may work for some types of bacteria and in certain fluids that will permit the bacterial concentration to substantially increase in the fluid sample incubated within the BacterioScan 216R device over a longer period of time (e.g., 8 hours).

Figure 16A:
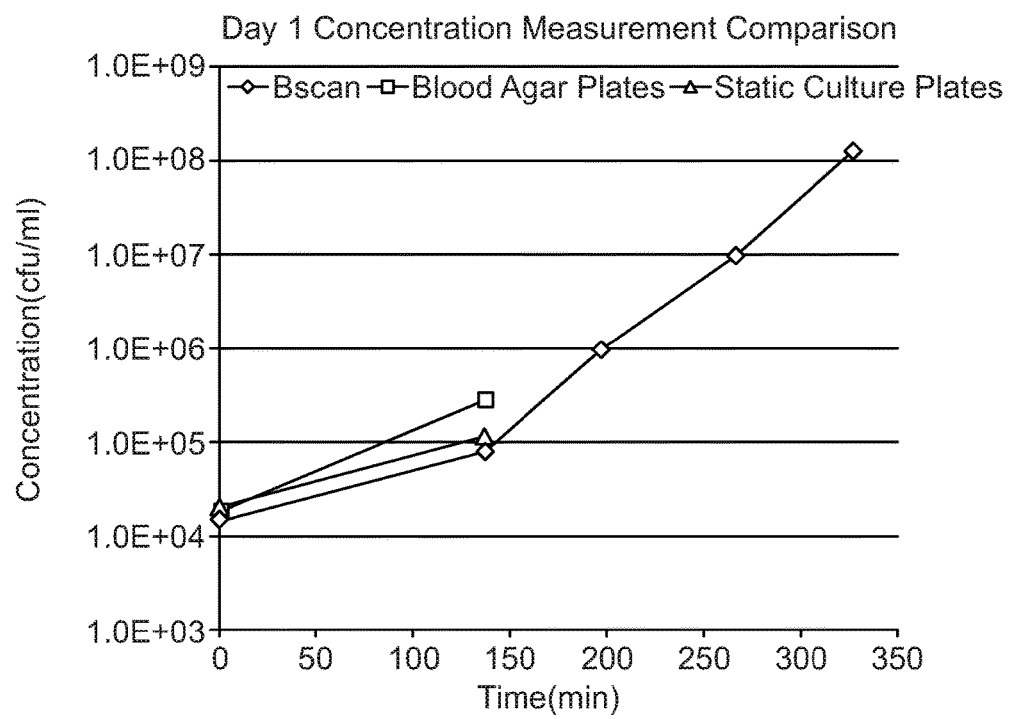
FIG. 16A illustrates Day 1 Test Results showing the incubating and optical-measuring device of FIG. 1 is measuring the proper concentration of bacteria within a fluid sample.
Figure 16B:
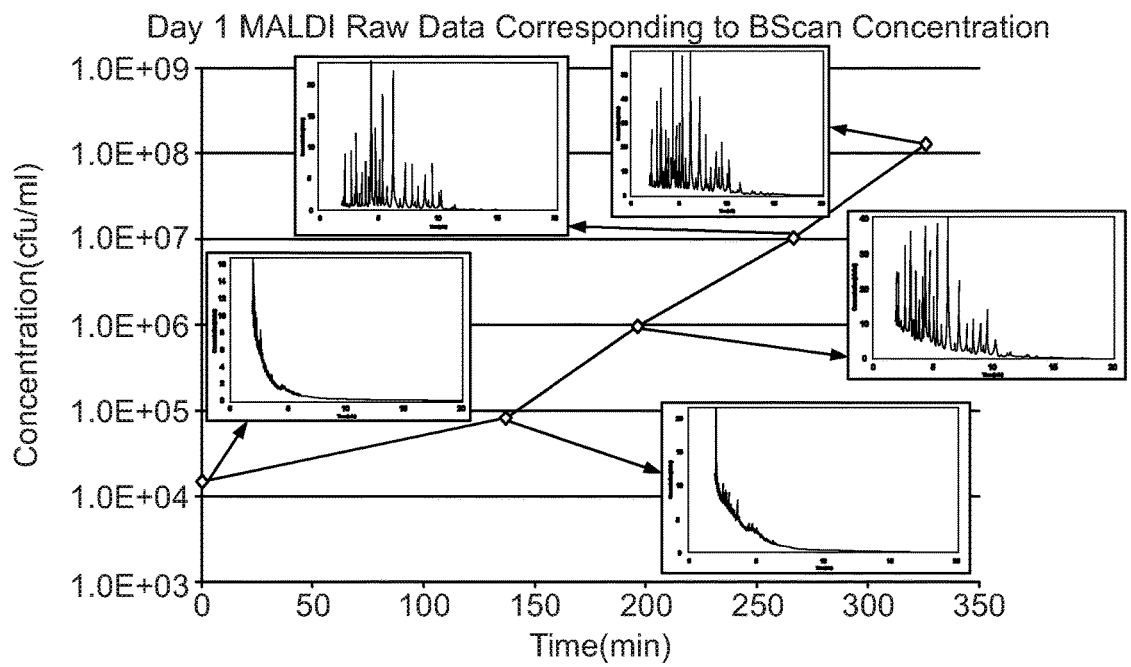
FIG. 16B illustrates the MALDI raw-data output for Day 1 ("Dry Target" test) at various bacterial concentrations as measured by the optical-measuring device of FIG. 1.

FIGS. 16A and 16B illustrate the results from Day 1. In particular, FIG. 16A illustrates the fact that the bacteria concentrations measured by the BacterioScan 216R device ("Bscan" from FIG. 1) were relatively consistent with the bacteria concentrations on the blood agar plates and the static culture plates. Accordingly, the bacteria concentrations measured by the BacterioScan 216R device are accurate for the purposes of the testing in Day 1. The concentration data for blood agar plates and static culture plates after 150 minutes are incomplete due to high/TNTC colonies. Each data point on FIG. 16A represents the time and concentration levels at which the fluid samples were processed and loaded onto MALDI.

FIG. 16B illustrates the MALDI raw data for the "dry target" samples at certain bacteria concentrations measured by the BacterioScan 216R device. For the first two data points, which correspond to bacteria at the $1 \times 10^4$ CFU/ml concentration level and the $1 \times 10^5$ CFU/ml concentration level, the results were not reliable for determining for genus identification or species identification. For the third data point, which corresponds to bacteria at the $1 \times 10^6$ CFU/ml concentration level, the results allowed the genus identification to be secured, but the bacterial species identification was only probable. For the fourth and fifth data points, which correspond to bacteria at the $1 \times 10^7$ CFU/ml concentration level and the $1 \times 10^8$ CFU/ml concentration level, the results were reliable for determining the bacterial genus identification and the species identification was highly probable.

Figure 17A:
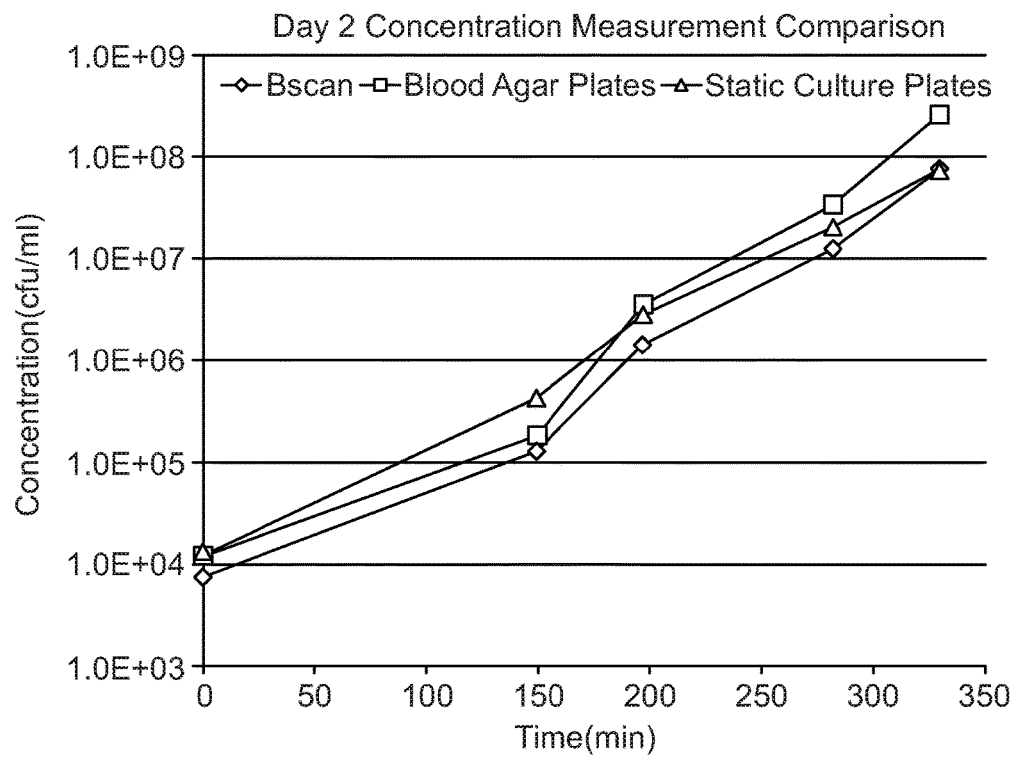
FIG. 17A illustrates Day 2 Test Results showing the incubating and optical-measuring device of FIG. 1 is measuring the proper concentration of bacteria within a fluid sample.
Figure 17B:
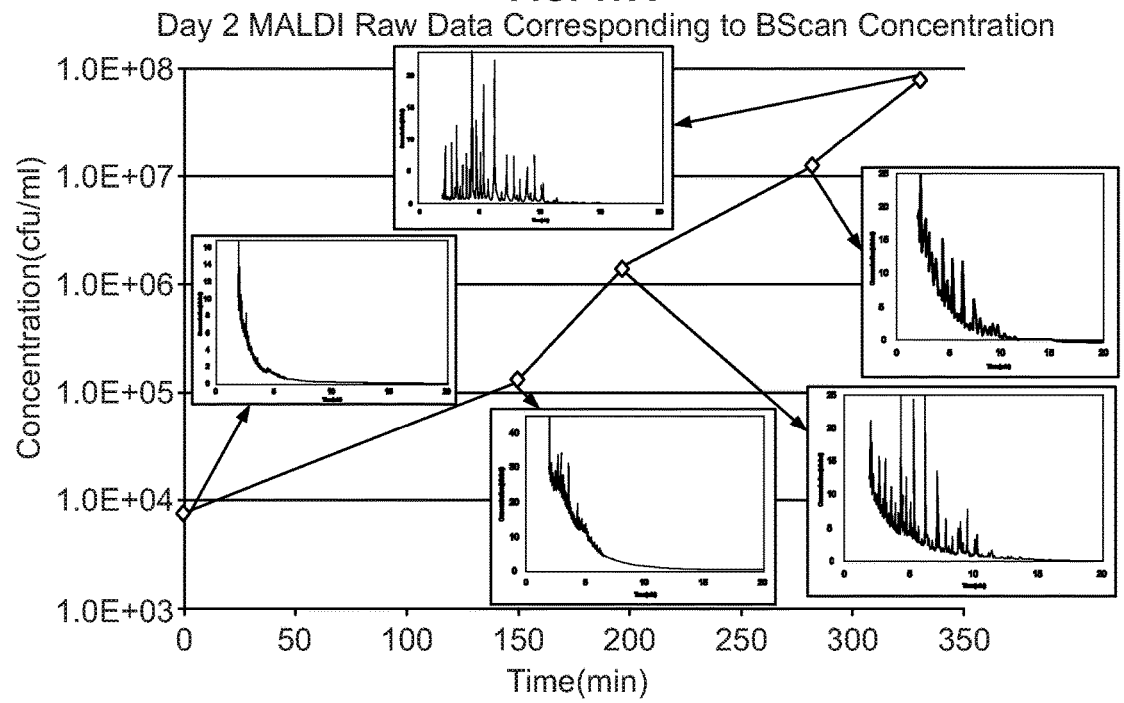
FIG. 17B illustrates the MALDI raw-data output for Day 2 ("Dry Target" test) at various bacterial concentrations as measured by the optical-measuring device of FIG. 1.

FIGS. 17A and 17B illustrate the results from Day 2. In particular, FIG. 17A illustrates the fact that the bacteria concentrations measured by the BacterioScan 216R device (FIG. 1) were relatively consistent with the bacteria concentrations on the blood agar plates and the static culture plates. Accordingly, the bacteria concentrations measured by the BacterioScan 216R device are accurate for the purposes of the testing in Day 2.

FIG. 17B illustrates the MALDI raw data for the "dry target" samples at certain bacteria concentrations measured by the BacterioScan 216R device. The results were consistent with Day 1 testing. For the first two data points, which correspond to bacteria at the $1 \times 10^4$ CFU/ml concentration level and the $1 \times 10^5$ CFU/ml concentration level, the results were not reliable for determining for genus identification or species identification. For the third data point, which corresponds to bacteria at the $1 \times 10^6$ CFU/ml concentration level, the results allowed the genus identification to be secured, but the bacterial species identification was only probable. For the fourth and fifth data points, which correspond to bacteria at the $1 \times 10^7$ CFU/ml concentration level and the $1 \times 10^8$ CFU/ml concentration level, the results were reliable for determining the bacterial genus identification and the species identification was highly probable.

As can be seen by the graphs of the MALDI raw data in FIGS. 16B and 17B, when the bacteria concentration (as measured by instrument 10, the BacterioScan 216R instrument) reaches $1 \times 10^6$ cfu/ml and the subsequent washing/centrifuging process is used on the liquid samples to achieve the "dry target" pellets, the MALDI device was able to identify the type of bacteria. In other words, at T=0, the concentration of the *e. coli* bacteria was initially $1 \times 10^4$ cfu/ml. Through the incubation process associated with the instrument 10 (BacterioScan 216R) the growth of bacteria over approximately 200 minutes caused the concentration of the bacteria to reach $1 \times 10^6$ cfu/ml, which was enough concentration of bacteria to result in the subsequently derived "dry target" samples to permit a reliable identification of the bacteria through the MALDI device. When the bacterial concentration went beyond the $1 \times 10^6$ cfu/ml level, the probability of identifying the bacteria was even greater. As such, the forward-scatter signal measurement associated with the instrument 10 (BacterioScan 216R device) provides periodic growth information to determine the concentration of the bacteria over time, allowing for the detection of a predetermined bacterial concentration. Again, it should be noted that a bacteria concentration of approximately $1 \times 10^4$ cfu/ml is considered the minimum bacterial concentration for a urinary tract infection, and most human samples that have a urinary infection are higher than the $1 \times 10^4$ cfu/ml bacterial concentration.

Figure 18:
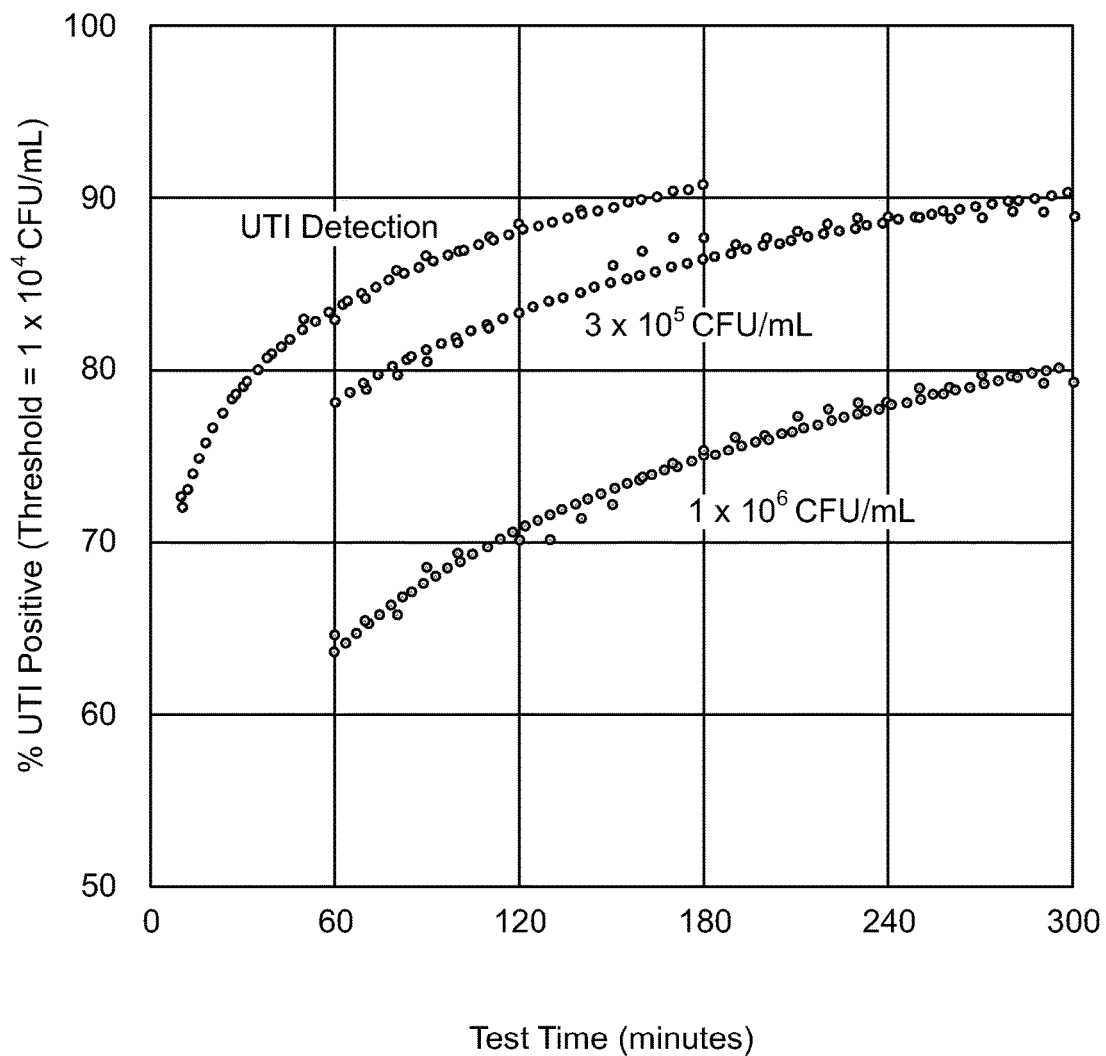
FIG. 18 illustrates the times at which certain concentrations of bacteria are detected within a urine sample that has been placed in the optical measuring device of FIG. 1.

FIG. 18 illustrates the percentage of patients that have tested positive for urinary tract infections, which has been identified as having a threshold bacteria concentration of $1 \times 10^4$ cfu/ml. Data were collected over several months from over 1500 UTI specimens using the BacterioScan 216R device (FIG. 1). The data from the urine specimens was generally measured and gathered for 180 minutes, such that the graph lines between 180 minutes to 300 minutes in FIG. 18 are extrapolations. As can been seen from the upper curve ("UTI Detection" which is a $10^4$ cfu/ml concentration), as the incubation period increases, the number of patients that are identified as having a urinary tract infection also increases as the bacteria grows within the cuvettes stationed within the BacterioScan 216R device.

In FIG. 18, the bottom set of data corresponds to a bacterial concentration of $1 \times 10^6$ cfu/ml, which has been identified as the minimum amount of bacteria concentration that will permit bacteria identification through the "dry target" process using the MALDI device of Example 1 above, as shown in FIGS. 16-17. Focusing solely on the bottom set of data ($1 \times 10^6$ cfu/ml) of FIG. 18, within 60 min. of the test, approximately 65% of the patients who have a urinary tract infection have been identified and their bacteria concentration is at least $1 \times 10^6$ cfu/ml. Again, it should be noted that most human urine samples that are infected have a bacteria level that far exceeds the $1 \times 10^4$ cfu/ml, which corresponds to the top curve ("UTI Detection"). Accordingly, at T=60 minutes, the present invention contemplates the incubation and optical measurement instrument of FIG. 1 will report back to the user (e.g., through the display device 14 of the instrument 10 or on a computer display linked to the instrument 10) a listing of the fluid samples that identify the approximately 65% of the fluid samples that can now be tested via the MALDI device because they have a sufficient bacteria concentration. Other samples continue to reside within the incubation and optical measurement instrument 10, until the optical measurements associated with each of those samples indicates the bacteria concentration has finally achieved $1 \times 10^6$ cfu/ml. In other words, by 120 minutes, another 5-6% of the fluid samples will have a concentration level that is at least $1 \times 10^6$ cfu/ml, such that approximately 70% to 71% of all samples having a bacterial infection have been identified and can be further processed to identify the specific bacteria through the MALDI device. And by 300 minutes, approximately 80% of all samples with a bacterial infection have enough concentration of bacteria to permit the identification of the specific bacteria through the MALDI device. It should be noted that as of 300 minutes, the remaining 20% of patients' samples having a bacterial infection are still identified, but the level of the bacteria has not achieved the level of $1 \times 10^6$ cfu/ml so as to permit reliable identification via a "dry target" process within the MALDI device. As such, those remaining 20% of the samples may need to be "plated" for high-concentration bacterial growth over a longer time (24-48 hours) before placement within the MALDI device. However, the benefits of the present invention are substantial in that, unlike the current state-of-the-art which may take several days to identify the type of bacterial infection within the urine, 65% of the patients who have a urinary tract infection (i) can be determined as having a "positive" UTI through the use of the optical measurement device, and (ii) can have identified the exact bacteria that caused the infection (which leads to a more rapid intake of the appropriate antibiotic or treatment plan). The overall process (including the 60 minutes of incubation time within the device) to identify the exact bacteria causing an infection is less than 2 hours.

The middle set of data in FIG. 18 (Labeled "$3 \times 10^5$ cfu/ml") represents a concentration level that is believed to be sufficient to permit the identification of the specific bacteria through the MALDI device by use of an enhanced washing and centrifuging process. The enhanced process may include methods of filtration or selective binding elements that can be used to concentrate one species of bacteria preferentially to another within a single liquid sample, or a highly specific lysing or antimicrobial chemoeffector, bacteriophage, or other natural or synthesized genetic agent, which may destroy or suspend the growth of a particular bacteria while leaving other unidentified bacteria unaffected, thereby reducing the prevalence of any known contaminant or other known organism and increasing the relative concentration of an unidentified organism so as to improve the probability of accurate detection by MALDO-TOF or other method. This will result in a higher concentration of bacteria that is placed as a "dry target" in the MALDI device. As such, the present invention contemplates a process by which 80-90% of the patients who have a urinary tract infection (i) can be determined as having a "positive" UTI through the use of the optical measurement device, and (ii) can have identified the exact bacteria that caused the infection within 2-3 hours. As such, relative to present practice, the inventive process results in 80-90% of patients have a UTI being treated much more quickly with the appropriate antibiotic or treatment plan.

There are a few additional noteworthy details of the system and process of FIGS. 11-18. First, the onboard incubation and growth monitoring of the instrument 10 detects low (T=0) infections and slow growing pathogens such that the detection can be after the initial laser scan, or shortly thereafter. And, the broth-dilution protocol reduces relative concentration of contaminants, chemical preservatives and/or residual antibiotics in the patient sample, and thereby reduces the lag time for the sample to enter into logarithmic growth rates resulting in earlier detection, as well as a measured growth rate that is more consistent than in the case of undiluted sample with unknown antibiotics or preservatives, providing additional information for deductive identification of the infective organism. Lastly, improvements in the extraction efficiency of the bacteria into the "dry target" pellets will speed results.

Figure 19:
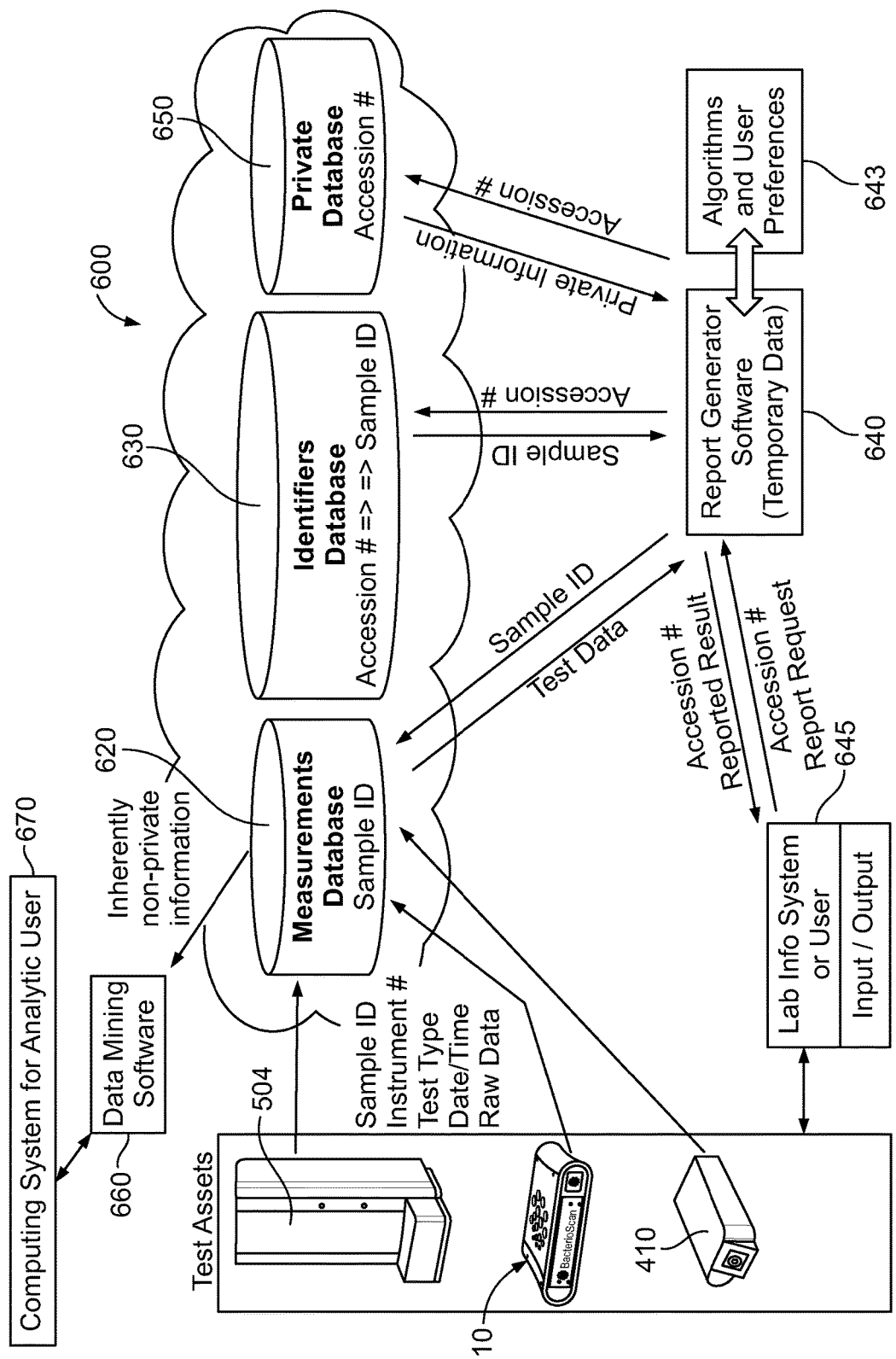
FIG. 19 is a schematic of a network that can be used to collect raw data from biological tests, such as testing involving the instruments of FIGS. 1-18, in which the raw data is maintained in a separate database that lacks patient identification information for data-mining analytics.

FIG. 19 illustrates a network 600 of digitally connected components that include one or more test instruments 10, 310, and 410 and mass spectrometers 504 (which may be coupled to the instruments 10 in accordance with FIGS. 13-18), test setups, and/or remote workstations that generate measurement data (collectively "Test Assets"). The digital network 600 further includes at least two independent databases—a measurements database 620 of raw collected measurements from the Test Assets and an identifiers database 630 that correlates the private event record (e.g., Accession Numbers) to a data record identifier, such as a Sample ID. The network 600 further includes a report-generator software module 640 that generates an interpreted result by correlating data from both the measurements database 620 and the identifiers database 630. The report-generator software module 640 analyzes the raw data and, by use of the correlated information in the identifiers database 630, delivers a report to the user via the Laboratory Information Systems ("LIS") 645, which includes user input devices and output devices, preferably in a manner such that it does not create or store a permanent record of the correlated information.

The report-generator software module 640 (or a separate sample-loading software program) may be used to collect an Event Record for storage into the Identifiers Database 630. The Event Record is an entry stored in the Identifier Database 630 that includes the Accession Number (or other hospital or facility record information) and the Sample ID, which as described in more detail below, includes the serial number and chamber number for the cuvette assembly 110 as indicated by a coded label 170 (FIG. 6). In common practice, the Accession Number is part of the hospital's or facility's patient record and is within the associated LIS 645. The Event Record may also include other data about the loading of the sample (e.g., time, date, loader, testing protocol). The following is an exemplary Event Record:

Date: Apr. 20, 2015

-continued

Time: 3:35:44 GMT
Hospital Accession Number: MB042015-033
Lab Operator: 056 (Jane Q. Biotech)
Sample ID: 023409823402934 (Cuvette Assembly serial #) −1 (chamber #)
Test Type: Urinary Tract Infection Diagnostic, 5 μm filter, no preservative, no yeast The Accession Number is typically recorded in the hospital's patient health record. The Sample ID would not be part of the hospital's patient health record. It should be noted that the Event Record could be recorded by a manual process in which the laboratory enters the appropriate data.

The Sample ID can be collected from the cuvette assembly 110 by use of a code reader (such as a barcode or QR-code reader) that reads the code 170, or the operator can simply type in the data read by eye. Alternately, the Sample ID could be generated by a random number generator and stamped onto a barcode label and stuck to the cuvette assembly 110, which disconnects the cuvette assembly 110 and all of its informational markings from the hospital identifications so as to further assure that the instrument 10 can never have any patient-identified information.

Within the network 600, the instruments 10 (and other Test Assets) only transmit raw measurement data to the measurements database 620. The interpretation of the measurement data from the instrument 10 and the reporting are conducted by the report-generator software module 640. This interpretation of the measurement data from the instrument 10 is accomplished by collecting the raw data from the Measurements Database 620, and then performing calculations and analysis using that data to determine results for the patient (e.g., Patient has a urinary tract infection, or Patient does not have a urinary tract infection). The formulas, algorithms, and reporting formats that the report-generator software module 640 uses to conduct these analyses are established by Algorithms and User-Preferences module 643, which may be stored in some other database. The Algorithms and User-Preferences module 643 is helpful because different laboratories may have different thresholds for what is a positive result (infection) versus a negative result (no infection) depending on the patient, the location (nursing home vs. surgical suite), or the loading protocol or notes (e.g., "this sample was bloody and required multiple filtering steps"). Hence, the Algorithms and User-Preferences module 643 provides the ability to select from different analytical methods, and possibly to even look at a set of measurements under several different analyses methods at different times. Because the network 600 does not rely on the instrument 10 (or any Test Asset) to provide a final test result (i.e., the instrument 10 only provides the raw measurement data that is stored in the measurements database 620), the network 600 provides the option to analyze the patient's sample multiple times (perhaps at points later in time than the initial test) under different analytical protocols because the report-generator software module 640 can retrieve different optional settings from the Algorithms and User-Preferences module 643. The LIS 645 permits the user to provide inputs and view/retrieve outputs (on a display or in paper) by use of the report-generator software module 640.

As shown in FIG. 19, the report-generator software module 640 and the User-Preferences module 643 can be stored locally within the laboratory and updated as needed. Alternatively, report-generator software module 640 and the Algorithms and User-Preferences module 643 are remotely located, such as in a remote cloud databases (like the separate databases 620, 630, and 650). The laboratory user then accesses the report-generator software module 640 and hence Algorithms and User-Preferences module 643 via a Java applet that is temporarily running its Graphical User Interface (GUI) on the user's laboratory computer, while the software and settings are remotely stored and running. As such, the network 600 can be hosted remotely and is accessible via the user's laboratory computer or tablet, via an app.

The network 600 may include a third database 650 ("The Private Database") that contains additional patient or potentially private information that is indexed to the Accession Number and protected as if it is Patient Identifiable Information (PII). The report-generator software module 640 may access, retrieve, and use this information in the process of analysis for interpretation, or for assembling a report that is specific to the patient. The report-generator software module 640 may generate or modify this third database 650 with interpreted results, raw data, or a record of an interpretation event or generation of a report (e.g., an event log).

A data-mining software module 660 is used to search or aggregate large amounts of raw test data from the measurements database 620, including the test type, the measured results, the date of test, and/or the identity of the Test Asset (e.g., the instrument 10). The data-mining software module 660 may analyze the data for improving the quality or utility of the collected data, or for improving future use of the network 600 or data within the network 600 for purposes such as public health surveillance, or for other purposes. Within the network 600, this data-mining software module 660 would not access any of the data from the Identifier Database 630 or the Private Database 650. Therefore, the data used and the results generated by the data-mining software module 660 would be devoid of any private information or information that could be combined or construed to be private information. As such, the network 600 would permit data analysis without the burdens placed to protect potentially private information.

Figures 20, 21:
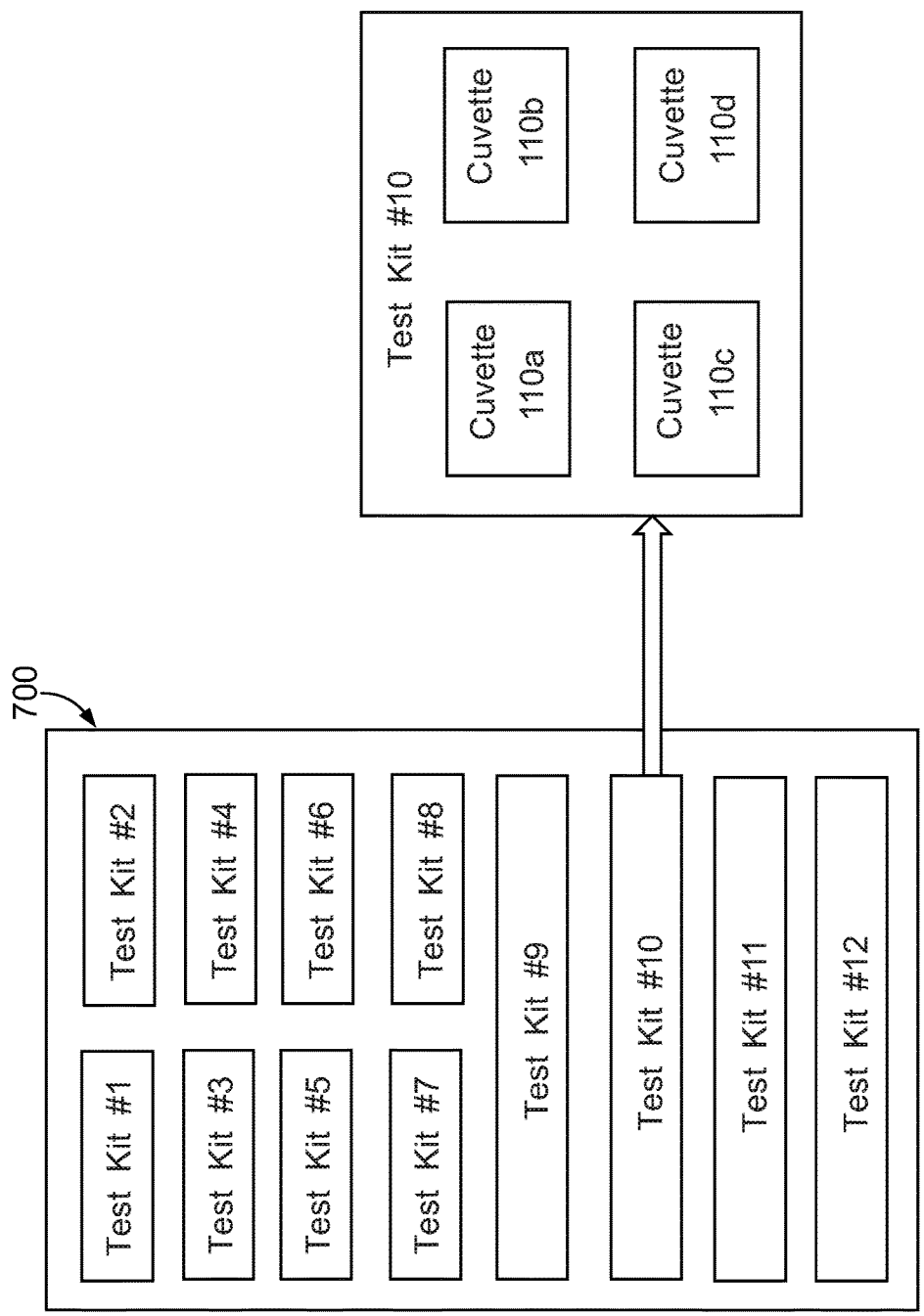
FIG. 20 is a schematic of an inventory of different test kits that can be received samples from patients and be used in connection with the test instruments.
FIG. 21 is a schematic of one test kit from FIG. 20 which includes four different cuvettes assemblies that is to be used for a particular type of testing.

One exemplary use of the network 600 will be described relative to FIGS. 19-21 with reference to the instrument 10 and the cuvette assemblies 110 described in FIGS. 1-8. A first patient is suspected of having a urinary tract bacterial infection and a fluid sample from the first patient is delivered to the laboratory for testing. With reference to FIG. 20, the laboratory technician receiving the fluid sample for the first patient is instructed to select a certain test kit from an inventory of test kits 700 that is to be used for the suspected urinary tract infection. In this case, the laboratory technician is instructed to select Test Kit #10 from an inventory 700. Test Kit #10 includes four cuvettes assemblies 110a, 110b, 110c, and 110d as shown in FIG. 21. Each of the four cuvettes assemblies 110a, 110b, 110c, and 110d includes a preloaded type and amount of chemoeffectors (e.g., antibiotics) that could be used for treating the suspected type of urinary tract infection in the first patient. One of the assemblies 110 may include one or more control chambers that lack a chemoeffector. The laboratory technician then loads (perhaps after a filtering procedure) each of the sixteen chambers within the four cuvettes assemblies 110a, 110b, 110c, and 110d with the fluid sample from the patient.

Each of the Test Kits #1-12 in FIG. 20 includes one or more cuvette assemblies 110 and is directed to a certain testing protocol. One or more chemoeffectors are present, and/or the same chemoeffectors may be present at different concentrations in the various chambers (as shown in the chemoeffector results of FIG. 12). In one preferred embodiment, an experimental chemoeffector (e.g., experimental drug) may be present in the one of the cuvette assemblies 110 of a Test Kit so that it can be tested against commonly used drugs. Further, one cuvette assembly 110 (or one or two chambers of one cuvette assembly) may include a chamber as a control for the test, which includes no chemoeffectors.

Regarding the identification of the cuvette assemblies 110, each of the cuvettes assemblies 110a, 110b, 110c, and 110d preferably includes the coded label 170 (FIG. 6) that can be scanned by the laboratory technician prior to placement in the instrument 10 via the door 12 (FIG. 1) or can be read via an internal scanning/reading device within the instrument 10. The code or code(s) on the coded label 170 correspond to the testing used for Test Kit #10, which is focused on the suspected urinary tract infection. A first type of information from the coded label 170 identifies the specific cuvette assembly 110 and its chamber that is being used, which together form the "Sample ID" show in FIG. 19. The Sample ID may also include the chemoeffector content within the chamber. A second type of information from the coded label 170 instructs the instrument 10 regarding the test protocol, such as the incubation temperature, test duration, and time intervals between taking test data by use of the laser 20 and the sensor 22 of the instrument 10. The laboratory technician also enters the Accession Number associated with the first patient via the LIS 645. The Accession Number is indexed to the Sample ID (e.g., cuvette assembly serial number and chamber number), which together comprise the Event Record. The software module 640 then sends the Accession Number and corresponding Sample ID to the identifiers database 630 for storage as an Event Record. To the extent a separate private database 650 is used as part of the network 600, the network 600 may store the Accession Number along with other private information related to the first patient.

The instrument 10 then performs the testing on the first patient's liquid sample within the cuvette assemblies 110a, 110b, 110c, and 110d. The raw data measurements for the testing from the instrument 10, including bacterial concentration data (e.g., bacterial concentration curves) over a period of time, are then stored within the measurements database 620. It is noteworthy that the measurements database 620 lacks any personal information regarding the patient. Rather, it includes information regarding the type of cuvette assemblies 110a, 110b, 110c, and 110d that have been tested, the chemoeffectors (e.g., antibiotic) contents of the cuvettes, and the raw data from the testing within the instrument 10. Considering that the measurements database 620 is storing information from multiple remote laboratories in which the instruments 10 are being used, the measurements database 620 contains an abundance of important biological information and data that can be analyzed and reported through the data-mining software module 660 to an analytics user.

Meanwhile, after a test has been completed, the laboratory technician using the LIS 645 can access both the measurements database 620 and the identifiers database 630 by use of the report generator software module 640 (and the algorithms and user preferences module 643) to develop a report specific to the first patient whose fluid sample has been tested. The report can then be sent back to the hospital and/or doctors treating the first patient that indicates the results. The results can be presented in various forms such as, (i) the first patient has or does not have a urinary tract infection, (ii) the first patient has a urinary tract infection treatable by antibiotic X, (iii) the first patient has a urinary tract infection treatable by antibiotic X or antibiotic Y, (iv) the first patient has a urinary tract infection treatable by a first predetermined concentration of antibiotic X, and/or (v) the first patient has a urinary tract infection treatable by a first predetermined concentration of antibiotic X or a second predetermined concentration of antibiotic Y. The report can be developed and/or reported manually or automatically through the LIS 645 associated with the laboratory.

By use of the data mining software module 660, the network 600 provides access to non-private data derived from the instruments 10 (and other Test Assets) within the measurements database 620 that can be used for numerous functions related to determining and/or predicting the effects and results of various chemoeffectors, such as:

- Direct comparison of multiple antibiotics against a certain infection on fluid samples from a large population of patients
- Direct comparison of the same antibiotic at different concentrations against a certain infection on fluid samples from a large population of patients
- Direct comparison of a new drug against known drugs on fluid samples from a large population of patients
- Detection of the emergence of one or more incidents of resistant infection in any healthcare site or geographic region at any time
- Determination that a certain type of bacteria has become or may be becoming (i.e., a prediction) resistant to a certain antibiotic
- Determination that a certain type of bacteria in a certain geographical region has become or may be becoming (i.e., a prediction) resistant to a certain antibiotic
- Determination that a certain type of bacteria in a certain hospital or care unit has become or may be becoming (i.e., a prediction) resistant to a certain antibiotic
- Determination of the susceptibility or resistance of an infection pathogen to an antimicrobial agent, molecule, or combination or sequence of exposure of antimicrobial agent or molecule with or without the active involvement of the proximate healthcare providers or clinical microbiologist The data mining software module 660 is stored within a memory device within or accessible by a computing system 670 having various hardware components (e.g., processors) and/or software or firmware components, modules, or features. The computing system 670 may include a smartphone, a laptop, a tablet computing device, a personal computer, or the like. The computing system 670 can be connected to the measurements database 620 through a public or private network, such as the Internet. The computing system 670 includes one or more input devices for receiving inputs from the analytics user, and one or more display devices for displaying outputs to the analytics user.

The analytics user that accesses the data within the measurements database 620 via the data-mining software module 660 can input various queries to determine and predict trends by use of the raw test data within the measurements database 620. In particular, when the instrument 10 and the associated cuvettes assemblies 110 are tested as described above, the raw data includes the concentration of bacteria in the liquid sample over a period of time. As the bacteria grow during the incubation period, the concentration (i.e., the number of bacteria "particles") increases, resulting in a different forward-scatter signal. As such, this test data can be in the form of graphical curves of bacterial concentration versus time. Accordingly, the analytics user may include a query related to locating a certain slope of the curve at a certain point in time. For example, after two hours, if the slope of the curve begins to approach a horizontal asymptote, such that the slope is approaching zero, then the growth of the bacteria within the liquid sample has subsided. In that scenario, identifying the chemoeffector(s) and/or the concentration of the chemoeffector(s) that prohibited or inhibited bacterial growth would be predictive of future treatments for patients having a similar condition. Accordingly, the analytics user may input queries into the data-mining software module 660 to locate Sample IDs with raw data results in which (i) the bacterial growth curve has a certain slope during an initial period of time, (ii) the bacterial growth curve has a certain slope after a certain period of time after which the chemoeffector(s) has begun to inhibit the bacterial growth, (iii) the initial bacteria concentration is a certain level, (iv) the bacterial growth curve for the "control" test for that sample has a certain higher slope to indicate the presence of growing bacteria, (v) the samples are identified in which the difference between slope(s) for one or more chemoeffector(s) test(s) and the control test is above a certain threshold.

While the network 600 of FIG. 19 has been described in connection with the use of the instrument 10 and the associated cuvette assemblies 110, other test instruments (such as the instruments 410) can be used as well. As described above with reference to FIGS. 13-18, after bacteria is detected and confirmed in a control sample by one of the instruments 10, 410, the sample fluid can undergo a centrifuging process, and the concentrated bacteria is placed into a mass-spectrometry microbial identification device 504 that can be used to identify the type of bacteria that was within the original fluid sample (for example, a urine sample from a particular patient). As such, the Test Assets may include a mass spectrometer device 504, such as Biotyper Matrix Assisted Laser Desorption Ionization-Time of Flight Mass Spectrometer (MALDI-TOF) from the Bruker Corporation, or a Vitek® MS device from bioMérieux SA, such as those discussed relative to FIGS. 13-18. Other known devices that use a mass spectrometer to identify the type of bacteria can be used as well. The detected type of bacteria can also be sent to the measurements database 620 for storage such that queries from the data mining software 660 can be based on bacteria type.

Figure 22:
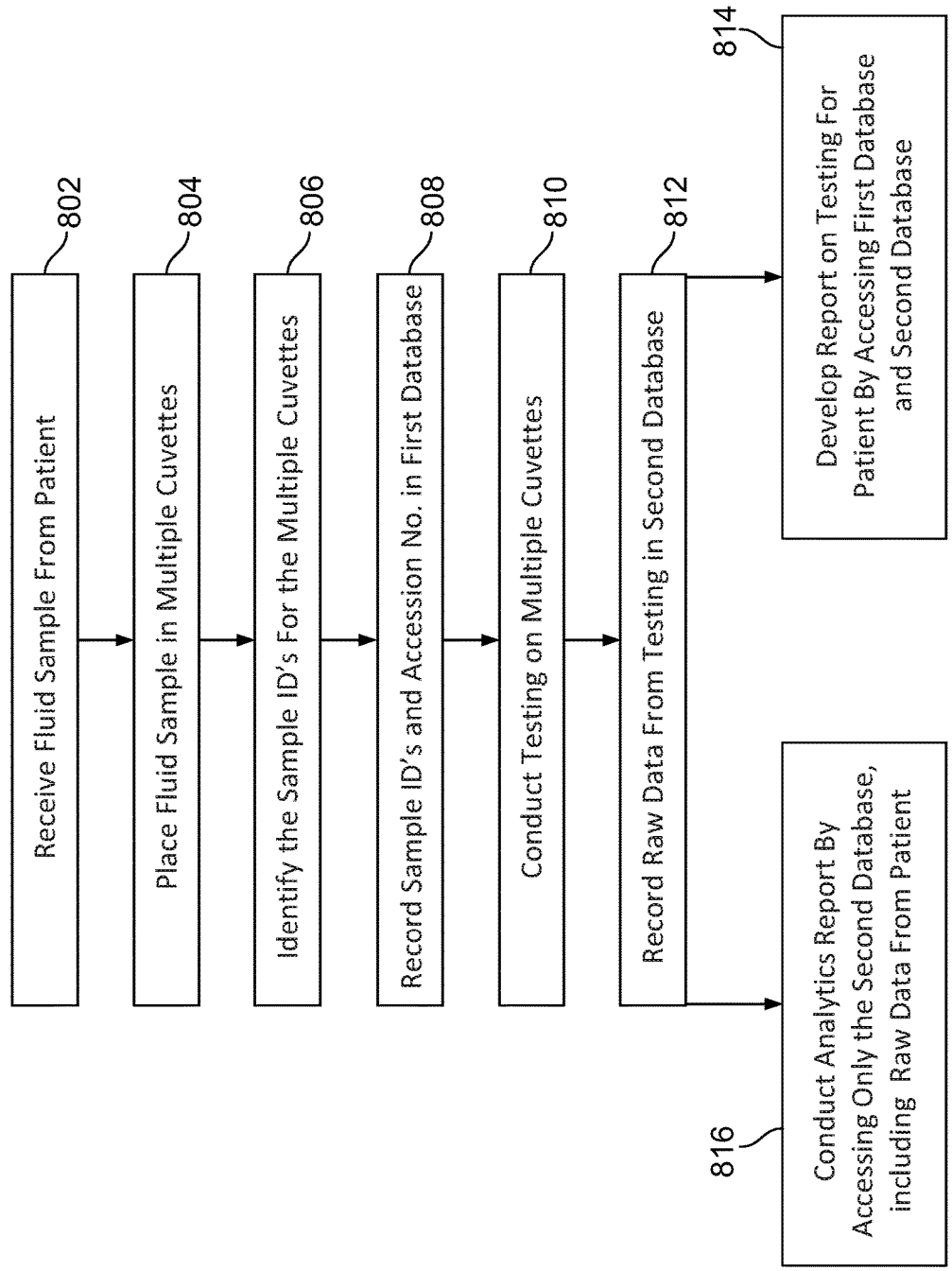
FIG. 22 is an exemplary flow diagram of the steps that can be used in conjunction with the network of FIG. 19.

FIG. 22 illustrates a flowchart that illustrates one method that can be used with the network 600 of FIG. 19. At step 802, a laboratory receives a fluid sample from a patient. At step 804, the fluid sample is placed in multiple cuvette assemblies 110 that can be used for testing, such as cuvette assemblies that can be used for optical forward-scattering measurement. At step 806, each of the cuvette assemblies 110 that will undergo testing that is identified with the Sample ID. Next, at step 808, the accession number associated with the hospital/patient and the Sample IDs to be used with the patient's fluid sample are stored in a first database. Next, the test is conducted on the multiple cuvette assemblies 110 at step 810. At step 812, the raw data from the testing on the multiple cuvette assemblies 110 is recorded in a second database that is different from and separate from the first database. At step 814, a report can be developed for the patient indicating the final result of the testing by accessing first database (which has the raw test results) and the second database (which has the accession number and the sample IDs). Finally, at step 816, because the second database does not contain any patient data, the raw test data from the first patient can be grouped together with other raw test data from other patients and accessed by data mining software to develop various analytics report.

Accordingly, the present invention relates to a network for medical diagnostic testing data where data is stored in a manner that is inherently untainted by patient identifiable information or any collection of data that might be construed to be private patient information. Data from instruments networked within such a system may be transmitted, stored, aggregated, analyzed, and re-interpreted without concern about patient privacy or data security, reducing the burdens of database and network design, operation, maintenance and use Additionally, it should be noted that the present invention contemplates a physical library of a plurality of test kits (e.g., test kits in FIGS. 20-21), wherein each test kit includes one or more cuvette assemblies 110 preloaded with chemo-effectors (and perhaps a control) that are designed for use in certain test protocols for different liquid samples suspected of having different types of bacterial content. Each test kit may include a code (e.g., the coded label 170 on the assembly 110) that dictates the test protocol (e.g., duration, incubation temperature, forward-scatter sensing time intervals) to be used by the instrument 10. Once the code 170 is inputted into the instrument 10 and the cuvette assemblies 110 are loaded into the instrument 10 via the door 12, the test can begin in accordance with the protocol. The raw test data from the instrument(s) 10 for a large population of the patients is stored as inherently non-private information within the measurements database 620 that is accessible to an analytics user via the computing system 670 to obtain important information regarding the determination of the results and/or the prediction of the effects of various chemo-effectors on bacteria.

Furthermore, the user may also be within a specific facility (e.g., a hospital) that accesses the measurements database 620 via the LIS 645 and uses the data mining software 660 locally to determine the test results on large samples of patients within that particular facility. Considering the benefits of the quick identification of bacterial infections by the instrument 10 (relative to typical plating techniques that take 24 to 48 hours), the user at facility is more capable of identifying an infectious disease outbreak with that particular facility. Consequently, the present invention contemplates a method of loading a plurality of patient samples in the cuvette assemblies 110, using the instrument(s) 10 to gather the samples' test data that is then stored in a database, and identifying, by accessing the database, a trend of bacterial infections within the particular facility. All of these steps can be performed in less than 24 hours, and oftentimes within 12 hours so as to avoid the need for the time-consuming "plating" steps. The steps may further include the process generally described relative to FIGS. 13-18 to identify the bacteria that is leading to the infections. Ultimately, this process permits the facility to utilize the appropriate antibiotics to quickly limit the spread of the infection within the facility.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

The invention claimed is:

1. An optical measuring instrument for determining a concentration of bacteria in a plurality of fluid samples, comprising:
   a housing with a substantially light-tight enclosure;
   a single cuvette assembly having a plurality of internals walls defining a plurality of individual internal fluid containers within the single cuvette assembly, each of the fluid containers holding a corresponding one of the plurality of fluid samples, each of the fluid containers having an input window and an output window, the single cuvette assembly including a code on an exterior surface thereof, the code providing information for a protocol for a test to be conducted by the optical measuring instrument on the fluid samples within the internal fluid containers within the single cuvette assembly;
   a platform structure located within the housing, the single cuvette assembly being registered on the platform structure;
   a laser located on an optical bench within the housing for providing an input beam for transmission into the input windows of the fluid containers and though the corresponding fluid samples, the input beam creating a forward-scatter signal associated with the concentration of bacteria, the laser periodically providing the input beam into each one of the fluid samples such that the multiple forward-scatter symbols are detected over a period of time for each of the fluid samples;
   at least one sensor located on the optical bench within the housing for detecting the forward-scatter signal exiting from the output windows;
   a code sensor for reading the information from the code on the single cuvette assembly;
   a heating element within the housing to maintain the fluid samples at a desired temperature to encourage bacterial growth in the fluid samples over a period of time, the desired temperature being defined by the protocol indicated by the code; and
   wherein the single cuvette assembly with the fluid containers is held in a fixed position and the optical bench undergoes translational movement so that the input beam from the laser sequentially addresses each of the plurality of fluid samples.

2. The optical measuring instrument of claim 1, wherein the heating element is part of an incubation system that further includes at least one temperature sensor for providing thermostatic control.

3. The optical measuring instrument of claim 1, wherein the single cuvette assembly with the individual fluid containers can be loaded through a door on the housing.

4. The optical measuring instrument of claim 1, wherein the number of multiple scatter signals for each of fluid samples is greater than twenty within a 2-hour test period.

5. The optical measuring instrument of claim 1, further including a display device coupled to the optical measuring instrument, the display device for displaying a bacterial growth curve for at least some of the fluid samples.

6. The optical measuring instrument of claim 5, further including an alarm for indicating when a bacterial growth curve exceeds a certain slope or the forward-scatter signal exceeds a certain value.

7. The optical measuring instrument of claim 1, wherein the single cuvette assembly includes a filter, the fluid sample passing through the filter before transmission of the input beam into the input windows.

8. An optical measurement system for use in optically measuring bacteria within a fluid sample, comprising:
   a light source for producing an input beam;
   a removable single cuvette assembly having a plurality of internal walls that define a plurality of internal fluid containers within the single cuvette assembly, the single cuvette assembly having individual windows associated with each of the plurality of fluid containers, the single cuvette assembly remaining in a fixed position within the system during operation, the single cuvette assembly including a code on an exterior surface thereof for providing information for a protocol for a test to be conducted by the optical measuring instrument on the fluid samples within the internal fluid containers of the single cuvette assembly;

a sensor for receiving a forward-scatter signal caused by the input beam passing through each of the plurality of fluid containers containing the fluid sample with the bacteria;

a heating system that permits a controlled incubation temperature for the fluid sample, the controlled incubation temperature during the test being indicated by information from the code; and a moveable optical bench undergoing translational movement, the light source and the sensor being mounted on the movable optical bench, the translational movement of the optical bench permitting the fluid samples within each of the plurality of fluid containers within the fixed single cuvette assembly to be sequentially placed into a path of the input beam such that the sensor receives multiple forward-scatter signals for each of the plurality of fluid samples over a period of time.

9. The optical measuring instrument of claim 1, wherein the code further provides information regarding a frequency of the optical measurements duration of the test.

* * * * *